(12) United States Patent
Li et al.

(10) Patent No.: US 10,788,474 B2
(45) Date of Patent: Sep. 29, 2020

(54) ONLINE MONITOR FOR TRACE SODIUM IN HIGH-PURITY WATER, AND ONLINE MONITORING METHOD AND DEVICE THEREOF

(71) Applicant: SHENZHEN ENER-CHEMISTRY INDUSTRIAL CO., LTD., Shenzhen (CN)

(72) Inventors: Jingye Li, Shenzhen (CN); Taohong Li, Shenzhen (CN); Taolin Li, Shenzhen (CN)

( * ) Notice: Subject to any disclaimer, the term of this patent is extended or adjusted under 35 U.S.C. 154(b) by 65 days.

(21) Appl. No.: 16/236,368

(22) Filed: Dec. 29, 2018

(65) Prior Publication Data
US 2019/0178864 A1    Jun. 13, 2019

Related U.S. Application Data

(63) Continuation of application No. PCT/CN2016/087781, filed on Jun. 29, 2016.

(51) Int. Cl.
*G01N 33/18* (2006.01)
*G01N 21/72* (2006.01)
(Continued)

(52) U.S. Cl.
CPC .......... *G01N 33/1826* (2013.01); *G01J 3/443* (2013.01); *G01N 21/274* (2013.01);
(Continued)

(58) Field of Classification Search
CPC ............................................... G01N 33/1826
(Continued)

(56) References Cited

U.S. PATENT DOCUMENTS 3,138,330 A * 6/1964 Gilber, Jr. ............ G01N 21/714
239/273
6,842,241 B2   1/2005 Harju et al.
7,449,294 B2   11/2008 Kriesel et al.

FOREIGN PATENT DOCUMENTS

CN       1560607 A    1/2005
CN       2694265 Y    4/2005
(Continued)

OTHER PUBLICATIONS

Internation Search Report of PCT/CN2016/087781, dated Mar. 1, 2017.

*Primary Examiner* — Tarifur R Chowdhury
*Assistant Examiner* — Omar H Nixon
(74) *Attorney, Agent, or Firm* — Erson IP (Nelson IP)

(57) ABSTRACT

An online monitor for trace sodium in high-purity water, and an online monitoring method and device thereof are provided. Under the control of an embedded industrial computer, an injection-calibration system conveys calibrated water samples and to-be-measured water samples to a flame atomization system continuously and stably. The flame atomization system forms a negative pressure field using a high-purity hydrogen-oxygen mixture as carrier gas, draws in the to-be-measured water samples for atomization, mixing and droplet separation, and then ignites a characteristic spectrum which emits sodium at a high-temperature inner cone. A photoelectric sensor system quickly scans the characteristic spectrum of sodium, and outputs a second-order differential modulation sodium spectrum after removing background interferences. A data acquisition system acquires an analog signal of the second-order differential modulation sodium spectrum, converts the analog signal into a digital signal and outputs the digital signal to the embedded industrial computer for real-time monitoring and control.

18 Claims, 12 Drawing Sheets

(51) Int. Cl.
*G01J 3/443* (2006.01)
*G01N 21/27* (2006.01)
(52) U.S. Cl.
CPC ......... *G01N 21/72* (2013.01); *G01N 33/1813* (2013.01); *G01N 2201/0484* (2013.01)
(58) Field of Classification Search
USPC ........................................................ 356/315
See application file for complete search history.

(56) References Cited

FOREIGN PATENT DOCUMENTS

| | | |
|---|---|---|
| CN | 101289747 A | 10/2008 |
| CN | 202361368 U | 8/2012 |
| CN | 102680454 A | 9/2012 |
| CN | 102928364 A | 2/2013 |
| CN | 103063654 A | 4/2013 |
| CN | 104198467 A | 12/2014 |

* cited by examiner

ONLINE MONITOR FOR TRACE SODIUM IN HIGH-PURITY WATER, AND ONLINE MONITORING METHOD AND DEVICE THEREOF

CROSS-REFERENCE TO RELATED APPLICATIONS

This application is a continuation of International Patent Application No. PCT/CN2016/087781 with a filing date of Jun. 29, 2016, designating the United States, now pending. The content of the aforementioned applications, including any intervening amendments thereto, are incorporated herein by reference.

TECHNICAL FIELD

The present disclosure relates to the field of online trace composition analysis instrument, and particularly relates to an online monitor for trace sodium in high-purity water, and a monitoring method and device thereof.

BACKGROUND OF THE PRESENT INVENTION

A sodium ion is one of important indicators for chemical supervision in a water supply treatment system, a boiler water supply system, a condensate treatment system and a steam (saturated steam and superheated steam) system of a thermal power plant and a commercial nuclear power plant. Harm of the sodium ion to a steam turbine has been confirmed by experimental study and supercritical unit operation experience, and the unit is developed towards high parameters (supercritical and ultra-supercritical) and large capacity. A corrosion process that occurs in the steam turbine has been proved by many research institutes. A considerable number of boiler tube burst and furnace pipes become brittle, and failure of the steam turbine is caused by corrosion. Several related chemical components exist in the corrosion process, wherein existence of a trace sodium ion is one of the direct reasons that cause this problem. In order to ensure safe operation of steam power equipment in the thermal power plant and the commercial nuclear power plant, online continuous monitoring for content of sodium ions in a water and steam system receives more and more attention. "Controlling sodium content in steam to be less than 1 μg/kg" is already a consensus of chemists in a supercritical thermal power plant and the commercial nuclear power plant.

At present, domestic and foreign methods for determining $Na^+$ content in water and steam in the thermal power plant and the commercial nuclear power plant mainly adopt an electrochemical monitor based on an ion-selective electrode principle. The theory of an ion-selective electrode technology is a Nerst equation based on a thermodynamic equilibrium principle, and an ion concentration (activity) is determined by virtue of a relationship between an electrode potential and the ion concentration (activity):

Nerst equation $$E = E_0 + \frac{2.3\pi RT}{nF} \log[Na^+] \qquad (1)$$

wherein E represents a measuring potential (mV), $E_0$ represents a reference potential (mV), R represents a perfect gas constant 8.31 (J/mol·R), T represents a temperature (K), n represents an ionic chemical valence, F represents a Faraday charge constant (F=96500 C/mol), and $[Na^+]$ represents sodium ion activity (the activity may be replaced with concentration while measuring trace sodium under the same temperature condition).

It should be concluded from the Nerst equation (1) that, the measuring potential (E) and a logarithmic value of the sodium ion concentration (activity) are in a linear relation under the condition that the reference potential ($E_0$) is stable. In addition, the slope of the linearity curve depends on the temperature of a measuring medium, and a zero point depends on the reference potential ($E_0$). Therefore, with respect to such sodium ion analyzers, accurate measurement for the measuring potential (E), the reference potential ($E_0$) and the temperatures (T) of the measuring medium and a reference medium is a precondition for ensuring measurement accuracy. Therefore, an online sodium analyzer based on the ion-selective electrode technology has defects as follows:

(1) Accuracy of a Measurement Result is Influenced by the Temperature of a Water Sample.

When water temperature deviates from 25° C., the accuracy of the measurement result may be seriously influenced by temperature change. Theoretically, the temperature may be automatically compensated by a temperature compensator of an instrument. However, the temperature is difficult in compensation, and then cost and complexity of the instrument may be increased.

(2) Accuracy of the Measurement Result is Influenced by a pH Value of the Water Sample.

Response of a sodium ion selective electrode to $H^+$ is more sensitive to $Na^+$. In order to eliminate the influence of the $H^+$ to determination of the $Na^+$, an alkaline reagent must be configured for inhibiting. In order to ensure the measurement accuracy of trace sodium, a pH value of the water sample with alkali must be 3 units larger than a value pNa. At present, almost all online sodium ion concentration analyzers increase the pH value of the measuring medium in a manner of adding diisopropylamine so as to effectively decrease the influence of the $H^+$ on measurement of $Na^+$ concentration. However, the diisopropylamine is an inflammable chemical having severe harm to the environment. Pulmonary edema may be caused in case of steam inhalation, and steam of the diisopropylamine has irritation to eyes. Moreover, the measurement result may be influenced by $NH_4^+$ and an amine ion if excessive alkaline reagents are added. $H^+$ may generate interference on the measurement result due to inadequate addition of the alkaline reagents. In order to regulate and control the dosage of a dosing system of the alkaline reagents, a complicated alkaline reagent regulation system must be added, thereby ensuring accurate determination of the sodium, increasing an uncertain factor and increasing the cost and complexity of the instrument.

(3) The Accuracy of the Measurement Result is Influenced by Flow Velocity of the Water Sample.

Electrical conductivity of water samples such as supplied water, condensate, steam and the like in the power plant is generally less than 0.2 μs/cm, similar to insulators. During measurement, the flowing water samples rub with the surface of the electrode to generate an electrostatic charge, and the charge is difficult to be conducted away in time. The electrostatic charge generated by such flow is accumulated on the surface of the electrode, so that the measuring potential deviates from a Nerst response potential, thereby seriously interfering and influencing the accuracy and reproducibility of the measurement result of the online sodium analyzer. Experimental results show that, the flow velocity of the water samples has a very great influence on the measurement result of the online sodium analyzer. Data in Table 1 shows that, when the flow velocity changes from 1 L/H to 4 L/H, a relative error of the measurement result is increased from 0.4% to 11%.

(4) The Accuracy of the Measurement Result is Influenced by a Liquid Junction Potential.

The liquid junction potential is generated by different ion diffusion rates on inner and outer sides of a contact interface when two solutions having different components or having the same component but different concentrations. When the liquid junction potential ΔE generates a potential error of 1 mW each time, a relative measuring error of 3.9% may be brought to the online sodium analyzer, while the liquid junction potential of an actual online sodium electrode measuring system is often up to dozens of millivolts, which indicates that the measuring error caused thereby is very large.

Therefore, the accuracy of the measurement result of the online sodium analyzer based on the ion-selective electrode is influenced by the temperature, the pH value, the flow velocity and the liquid junction potential of the water samples. With respect to the determination of the sodium in an extremely low concentration range, the measurement result is an almost constant random number, and the trace sodium in high-purity water cannot be subjected to online real-time, accurate and quick detection.

SUMMARY OF PRESENT INVENTION

In view of this, the purpose of the present disclosure is to provide an online monitor for trace sodium in high-purity water through second-order differential flame emission spectrometry, and a monitoring method and device thereof, so as to solve the technical problem that online real-time, accurate and quick detection of trace sodium in high-purity water cannot be realized.

The present disclosure adopts the following technical solution to solve the above technical problem:

According to one aspect of the present disclosure, a provided online monitor for trace sodium in high-purity water includes an injection-calibration system, a flame atomization system, a photoelectric sensor system, a data acquisition system and an embedded industrial computer which are connected successively, wherein the injection-calibration system is configured for continuously and stably conveying calibrated water samples and to-be-measured water samples to an inlet of an injection capillary pipe of a glass concentric pneumatic atomizer of the flame atomization system under the control of the embedded industrial computer;

the flame atomization system is configured for forming a negative pressure field by using a high-purity hydrogen-oxygen mixture as carrier gas which enters an atomizing nozzle throat of the glass concentric pneumatic atomizer, automatically drawing the calibrated water samples and the to-be-measured water samples from the injection-calibration system into an atomizing chamber for completing atomization, mixing and droplet separation, and then igniting the water samples at a high-temperature inner cone of an annular central porous burner to form a flame which radiates a sodium spectrum of 589.0 nm;

the photoelectric sensor system is configured for quickly scanning a characteristic spectrum of sodium, producing a second-order differential modulation sodium spectrum after removing background interferences, receiving the excitation of the second-order differential modulation sodium spectrum by a photomultiplier tube, producing second-order differential frequency-modulated current, and amplifying and outputting the current to the data acquisition system;

the data acquisition system is configured for acquiring an analog signal of the second-order differential frequency-modulated current, converting the analog signal into a digital signal and outputting the digital signal to the embedded industrial computer for real-time monitoring and control; and the embedded industrial computer is configured for conducting real-time control over the operation of the injection-calibration system, the flame atomization system, the photoelectric sensor system and the data acquisition system and analyzing and processing the acquired data in real time to obtain a test result.

According to another aspect of the present disclosure, a provided online monitoring method for trace sodium in high-purity water is applied to an embedded industrial computer and includes the following steps:

an ignition step: starting an electrolytic pure water hydrogen-oxygen generator, and starting an ignition electromagnetic valve after detecting that the output pressure of the electrolytic pure water hydrogen-oxygen generator reaches a preset ignition threshold and an automatic ignition power supply is normal;

a calibration step: controlling the injection-calibration system to convey the calibrated water samples to the flame atomization system continuously and stably after detecting that a flame sensor status signal is normal, and issuing a data acquisition instruction to a data acquirer to obtain measured data of the calibrated water samples acquired by the data acquirer;

a measurement step: controlling the injection-calibration system to convey the to-be-measured water samples to the flame atomization system continuously and stably after detecting that the connection between an injection three-way valve and a calibration switching electromagnetic valve is in a closed state, a water sample inlet regulating valve is in a turn-on state and the injection three-way valve is connected to a water inlet pipe of a constant-level overflow water sample cup; and obtaining measured data of the to-be-measured water samples acquired by the data acquirer; and a data processing step: conducting real-time statistical analysis on the measured data of the calibrated water samples and the measured data of the to-be-measured water samples to obtain a test result of the trace sodium.

According to still another aspect of the present disclosure, a provided online monitoring device for trace sodium in high-purity water is applied to an embedded industrial computer and includes the following modules:

an ignition module configured for starting an electrolytic pure water hydrogen-oxygen generator, and starting an ignition electromagnetic valve after detecting that the output pressure of the electrolytic pure water hydrogen-oxygen generator reaches a preset ignition threshold and an automatic ignition power supply is normal;

a calibration module configured for controlling the injection-calibration system to convey the calibrated water samples to the flame atomization system continuously and stably after detecting that a flame sensor status signal is normal, and issuing a data acquisition instruction to a data acquirer to obtain measured data of the calibrated water samples acquired by the data acquirer;

a measurement module configured for controlling the injection-calibration system to convey the to-be-measured water samples to the flame atomization system continuously and stably after detecting that the connection between an injection three-way valve and a calibration switching electromagnetic valve is in a closed state, a water sample inlet regulating valve is in a turn-on state and the injection three-way valve is connected to a water inlet pipe of a constant-level overflow water sample cup; and obtaining measured data of the to-be-measured water samples acquired by the data acquirer, and a data processing module configured for conducting real-time statistical analysis on the measured data of the calibrated water samples and the measured data of the to-be-measured water samples to obtain a test result of the trace sodium.

In the online monitor for trace sodium in high-purity water, and the monitoring method and device thereof provided by the present disclosure, elements are analyzed qualitatively and quantitatively through atomic emission spectrometry according to characteristic spectrums emitted when to-be-measured element atoms in an excited state return to a ground state; and the intensity of the characteristic spectrums of the elements is configured for quantification, thereby effectively overcoming the defects of an ion selective electrode method at the aspect of detection of the trace sodium and generating the following beneficial effects:

(1) The measurement result is stable and reliable: it is not affected by the water sample temperature, pH, flow velocity and other changes.

(2) High sensitivity: the present disclosure has the unique function of automatically eliminating continuous background interferences, can accurately measure weak spectral signals submerged in strong noise, and has a detection limit less than 0.1 µg/L.

(3) Low measurement cost: the measurement process does not require the addition of toxic and harmful chemicals such as alkalizers (diisopropylamine) and other expensive consumables (electrodes, internal reference solutions, electrode cleaning agents and activators).

(4) The instrument is simple in structure, low in cost and convenient in extensive popularization and application.

Realization of the purpose, functional characteristics and advantages of the present disclosure will be further described in combination with the embodiments and with reference to the drawings.

DETAILED DESCRIPTION OF PREFERRED EMBODIMENTS

To make the technical problem to be solved, the technical solution and the beneficial effects of the present disclosure more clear, the present disclosure will be further described below in detail in combination with the drawings and the embodiments. It should be understood that specific embodiments described herein are only configured for explaining the present disclosure, not configured for limiting the present disclosure.

Embodiment 1

Figure 1:
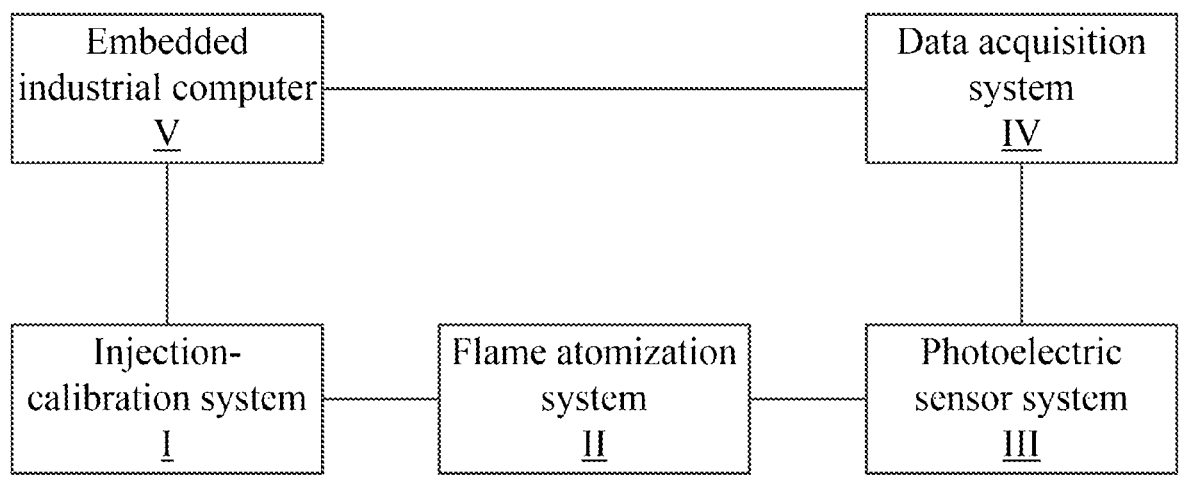
FIG. 1 is a structural block diagram of an online monitor for trace sodium in high-purity water provided in an embodiment of the present disclosure.
Figure 9:
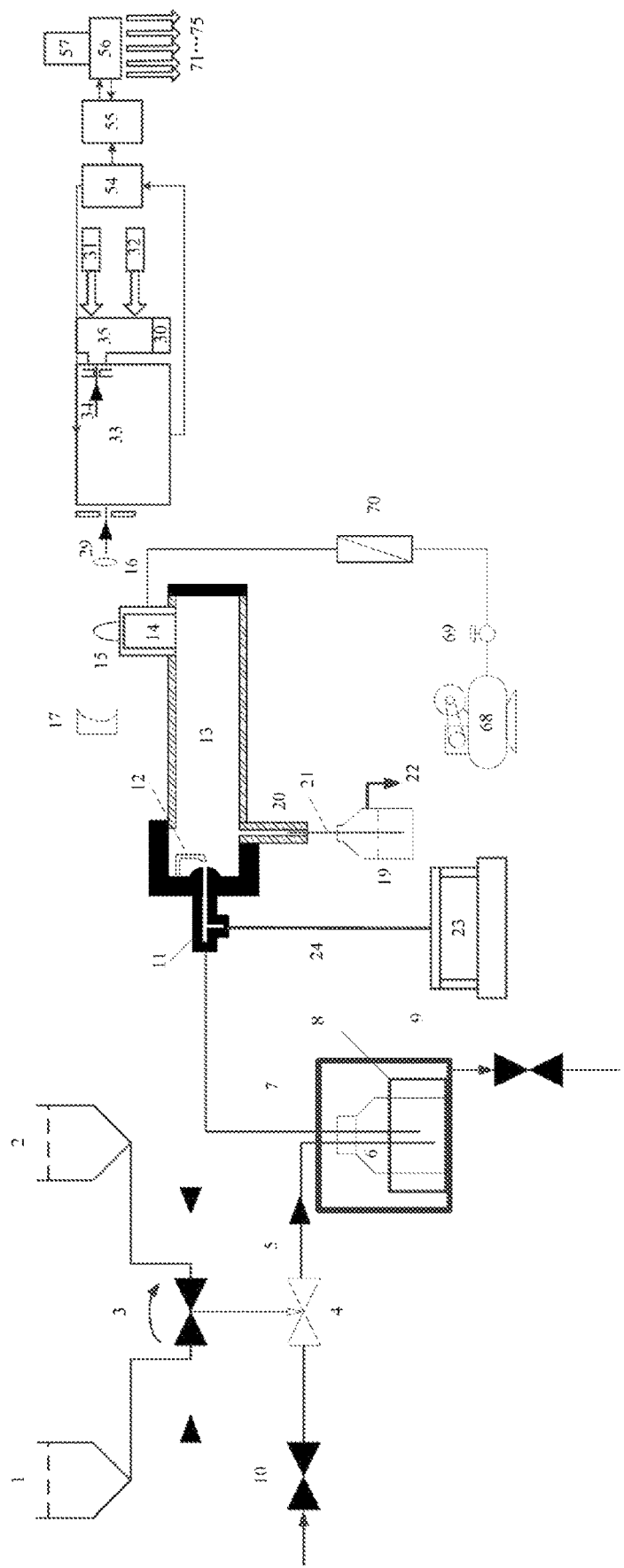
FIG. 9 is an overall structural schematic diagram of an online monitor for trace sodium in high-purity water provided in a preferred embodiment of the present disclosure.

As shown in FIG. 1 and FIG. 9, an online monitor for trace sodium in high-purity water provided in an embodiment of the present disclosure includes an injection-calibration system I, a flame atomization system II, a photoelectric sensor system III, a data acquisition system IV and an embedded industrial computer V which are connected successively.

The injection-calibration system I is configured for continuously and stably conveying calibrated water samples and to-be-measured water samples to an inlet of an injection capillary pipe of a glass concentric pneumatic atomizer of the flame atomization system under the control of the embedded industrial computer.

Specifically, flame emission spectrometry is a relative measurement method which uses a ratio of spectral linear radiation intensities of a measured sample to a prepared standard sample to determine the concentration of the measured sample. Before measurement by the instrument, a standard water sample similar to the upper control limit of sodium ion concentration in a measured water sample must be prepared to accurately calibrate the instrument. The injection-calibration system I successively executes a calibration procedure and a measurement procedure of the instrument under the control of an instruction issued by a CPU of the embedded industrial computer V to successively and stably convey high-purity water for calibration, standard water samples and to-be-measured water samples to the inlet of the injection capillary pipe of the glass concentric pneumatic atomizer, so that these functional water samples automatically enter the glass concentric pneumatic atomizer 11 through the injection capillary pipe and are atomized, and then enter a high-temperature inner cone to complete an atomization process and also emit a sodium characteristic spectrum of 589.0 nm.

The flame atomization system II is configured for forming a negative pressure field by using a high-purity hydrogen-oxygen mixture as carrier gas which enters an atomizing nozzle throat of the glass concentric pneumatic atomizer, automatically drawing the calibrated water samples and the to-be-measured water samples from the injection-calibration system into an atomizing chamber for completing atomization, mixing and droplet separation, and then igniting the water samples at a high-temperature inner cone of an annular central porous burner to form a flame which radiates a sodium spectrum of 589.0 nm.

The photoelectric sensor system III is configured for quickly scanning a characteristic spectrum of sodium, producing a second-order differential modulation sodium spectrum after removing background interferences, receiving the excitation of the second-order differential modulation sodium spectrum by a photomultiplier tube, producing second-order differential frequency-modulated current, and amplifying and outputting the current to the data acquisition system.

The data acquisition system IV is configured for acquiring an analog signal of the second-order differential frequency-modulated current, converting the analog signal into a digital signal and outputting the digital signal to the embedded industrial computer for real-time monitoring and control.

The embedded industrial computer V is configured for conducting real-time control over the operation of the injection-calibration system I, the flame atomization system II, the photoelectric sensor system III and the data acquisition system IV and analyzing and processing the acquired data in real time to obtain a test result.

Specifically, in the embodiments of the present disclosure, programmed analytical operations of continuous injection and intermittent static measurement are adopted. For example, a real-time water sample measurement is completed by performing a reading operation every 10 minutes. The injection valve is turned off by a computer program in the measuring process to realize static measurement of the constant-level overflow water sample cup, thereby ensuring real-time representativeness of the measurement result, stability of the measurement condition and repeatability of the measurement result. ARK-2120L-S 8A1E industrial control host without fan can be used as the embedded industrial computer. The embedded industrial computer has the main effect of controlling the whole data acquisition process as a control center of the whole data acquisition system. In the acquisition process, through the operation of data acquisition programs (software), the embedded industrial computer controls the data acquirer, can also calculate the data, and can realize the functions of real-time printing and output, image display, data storage and management, network transmission of the data, etc.

Embodiment 2

Figure 2:
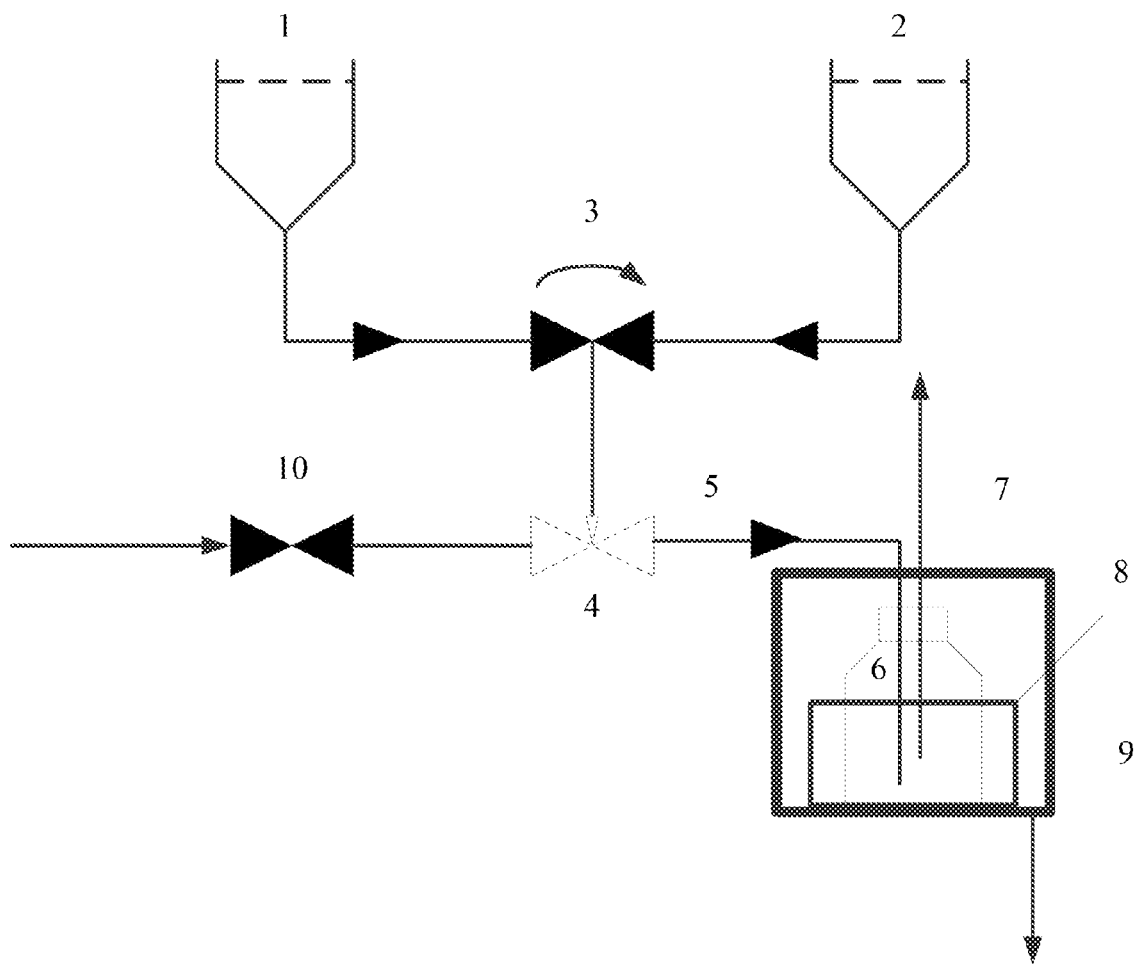
FIG. 2 is a structural schematic diagram of an injection-calibration system provided in a preferred embodiment of the present disclosure.

By referring to FIG. 2 and FIG. 9, an injection-calibration system provided in an embodiment of the present disclosure includes a high-level high-purity water cup for calibration 1, a high-level standard water sample cup for calibration 2, a calibration switching valve 3, an injection three-way valve 4, a water inlet pipe 5 of a constant-level overflow water sample cup 6, the constant-level overflow water sample cup 6, an atomizer injection capillary pipe 7, a cylindrical fixing groove 8 of the constant-level overflow water sample cup 6, an overflow water collection cup 9 and a water sample inlet regulating valve 10 from a boiler water-steam sampling rack.

The calibration switching valve 3 is a two-position three-way electromagnetic valve. Three channels are respectively connected with the high-level high-purity water cup for calibration 1, the high-level standard water sample cup for calibration 2 and the injection three-way valve 4. Another two paths of the three-way valve 4 communicated with the calibration switching valve 3 are respectively communicated with the water sample inlet regulating valve 10 and the water sample inlet pipe 5 of the constant-level overflow water sample cup 6. Each of the high-level high-purity water cup for calibration 1 and the high-level standard water sample cup for calibration 2 may be a bottom-opened polyethylene (PE) container having a capacity of 1000 mL. The bottom of the container is of a conical funnel structure, and a height difference between the bottom of the container and an inlet of the atomizer injection capillary pipe 7 is a second preset height difference (preferably about 1000 mm). The high-purity water for calibration is high-purity water configured for preparing a standard water sample for calibration at that time.

The water sample inlet pipe 5 of the constant-level overflow water sample cup 6 is inserted from a top overflow port of the constant-level overflow water sample cup 6 into the bottom of the constant-level overflow water sample cup 6. An outlet of the water sample inlet pipe 5 is lower than the inlet of the atomizer injection capillary pipe 7 by a first preset height difference (preferably about 10 mm). The atomizer injection capillary pipe 7 is connected from the bottom of the constant-level overflow water sample cup 6 to a water sample inlet of a glass concentric pneumatic atomizer 11 of a flame atomization system of hydrogen-oxygen mixture.

The constant-level overflow water sample cup 6 is preferably a 125 mL of standard PE narrow-mouth sampling bottle placed in the cylindrical fixing groove 8 in the center of the open overflow water collection cup 9. The cylindrical fixing groove 8 has a size of Φ52×50 (H). Flow velocity of a water sample flowing through the constant-level overflow water sample cup 6 is designed as 40 mL/min-60 mL/min. An overflow port of the constant-level overflow water sample cup 6 is a bottle opening of the 125 mL of standard PE narrow-mouth sampling bottle. Overflowing of the constant-level overflow water sample cup 6 has an effect of maintaining a stable liquid-column height of the water sample at the inlet of the injection capillary pipe 7 in a measuring process. By means of the stable water sample height, a static pressure at the inlet of the capillary pipe may be stable. By maintaining the stable static pressure at the inlet of the capillary pipe, lift of the water sample entering the atomizer may be stable under a stable pressure of carrier gas (hydrogen-oxygen mixture). The stable lift of the water sample can ensure a stable flame combustion temperature in the measuring process, thereby ensuring the stability and repeatability of the measurement result. Meanwhile, when the water sample overflows from the top of the constant-level overflow water sample cup 6, real-time property of the measured water sample in the constant-level overflow water sample cup 6 is ensured. This design ensures that the outlet of the water sample inlet pipe 5 is lower than the inlet of the atomizer injection capillary pipe 7 by the first preset height difference (about 10 mm), and ensures the real-time property of the water sample entering the injection capillary pipe, thereby ensuring the real-time representativeness of the measured data.

Embodiment 3

Figure 3:
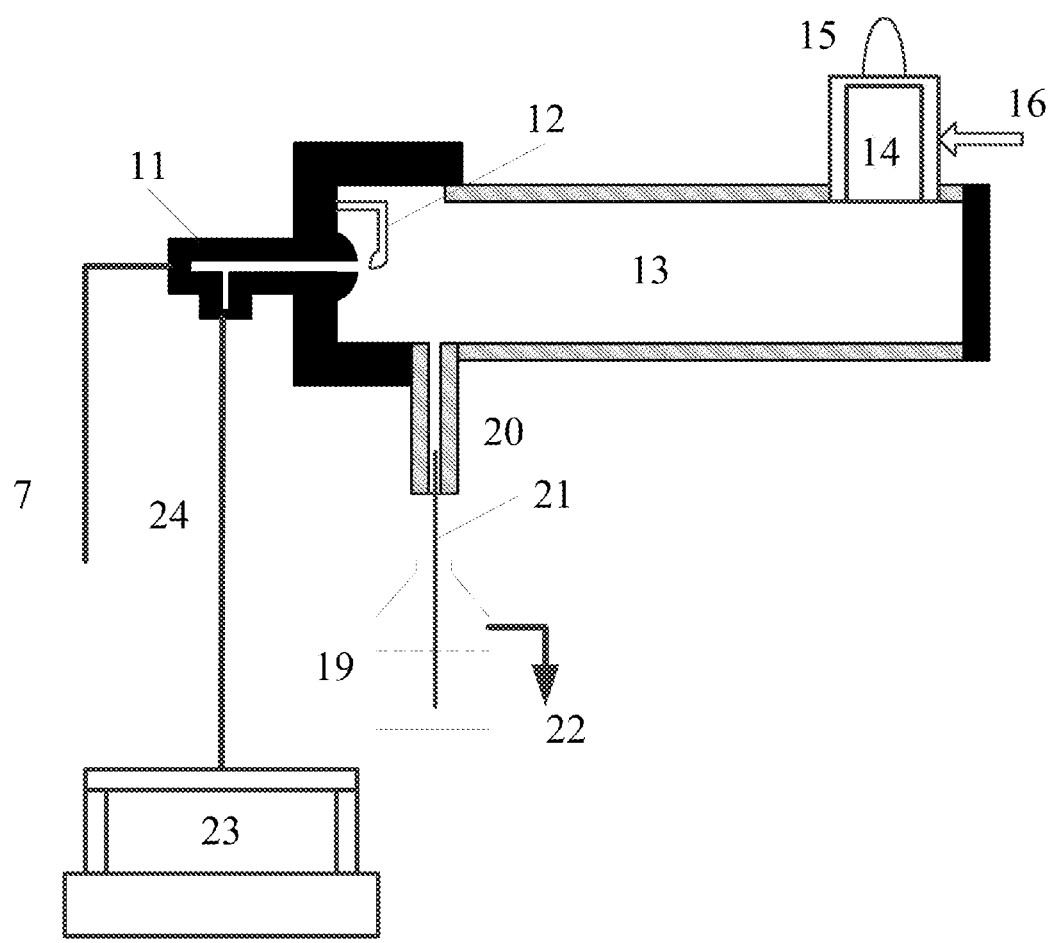
FIG. 3 is a structural schematic diagram of a flame atomization system provided in a preferred embodiment of the present disclosure.

By referring to FIG. 3 and FIG. 9, a flame atomization system of a hydrogen-oxygen mixture provided in an embodiment of the present disclosure includes a glass concentric pneumatic atomizer 11, atomizing chamber impact beads 12, an atomizing chamber 13, an annular central porous burner 14, a purified air annular passage inlet 16, a constant-level water seal device 19, an atomizing chamber wastewater outlet 20, an atomizing chamber wastewater discharge pipe 21, a constant-level water seal device overflow pipe 22, an electrolytic pure water hydrogen-oxygen generator 23 and an atomizer hydrogen-oxygen mixture (carrier gas) inlet pipe 24, wherein High-purity hydrogen-oxygen mixture having a volume ratio ($H_2/O_2$) of 2:1 produced by the electrolytic pure water hydrogen-oxygen generator 23 serves as carrier gas of the glass concentric pneumatic atomizer 11. Flow is preferably controlled to be 3 L/min to 5 L/min, and lift of the water sample is controlled to be 3 mL/min to 5 mL/min. The high-purity hydrogen-oxygen mixture is "gas-hydrogen" and is also "oxidant gas-oxygen". The mixture which is the "gas" and is also the "oxidant gas" is also the "carrier gas" of the atomizer. The "carrier gas" enters the atomizing nozzle throat of the atomizer to form a "negative pressure field", so that to-be-measured water samples from the constant-level overflow water sample cup 6 are automatically drawn into the atomizing chamber 13 via the injection capillary pipe 7 to complete the processes of atomization, mixing and droplet separation, and then are ignited above an outlet of a central porous burning head 25 of the annular central porous burner 14 to form a flame 15 that radiates a sodium spectrum of 589.0 nm.

The constant-level water seal device 19 is an open narrow-mouth polyethylene (PE) drum. The atomizing chamber wastewater discharge pipe is fixedly connected to the atomizing chamber wastewater outlet 20 by threads and vertically inserted into the narrow-mouth polyethylene (PE) drum. A distance between the bottom of the atomizing chamber wastewater discharge pipe 21 and the bottom of the drum is about 5 cm, and a distance between the bottom of the atomizing chamber wastewater discharge pipe 21 and a center of an open hole of the overflow discharge pipe is about 15 cm.

Figure 4:
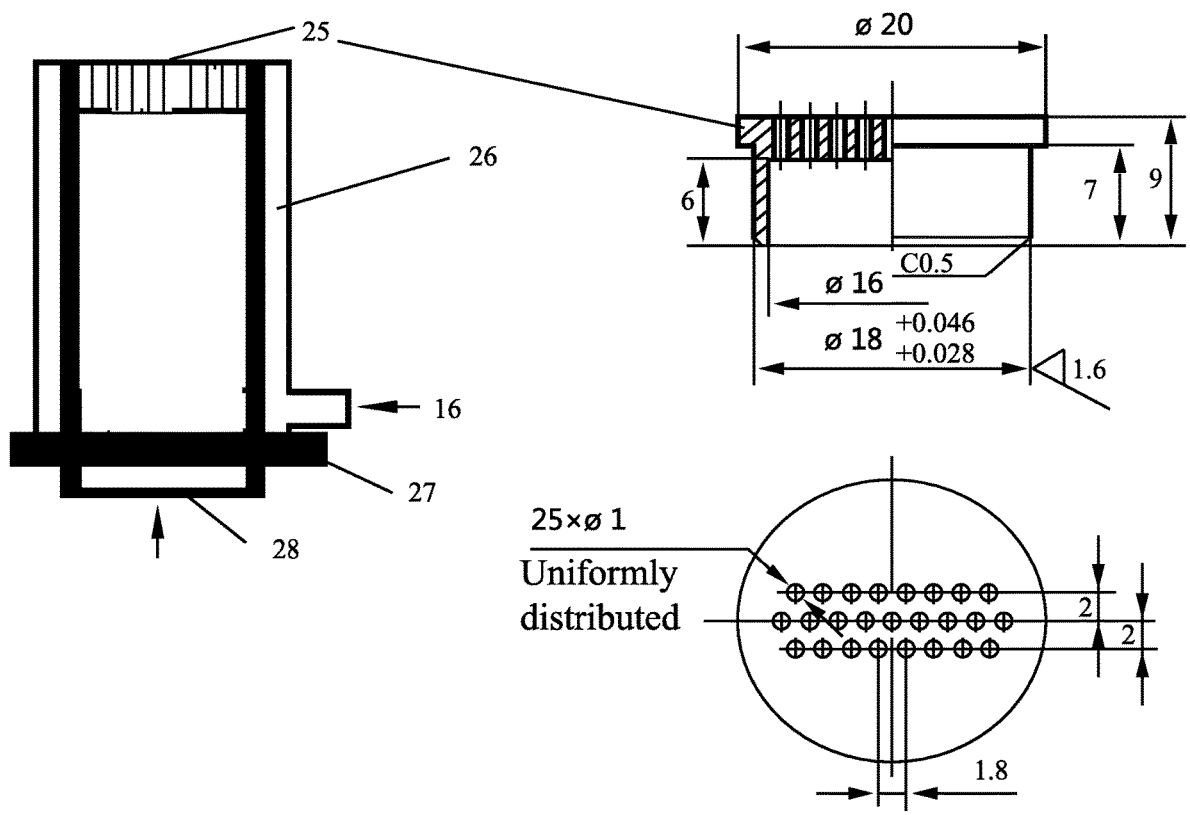
FIG. 4 is a structural schematic diagram of an annular porous burner provided in a preferred embodiment of the present disclosure.

By referring to FIG. 4 and FIG. 9, the annular central porous burner 14 is a full-titanium burner capable of producing purified air surrounding flames, and includes the central porous burning head 25, a purified air annular passage 26 disposed around the central porous burning head, a purified air inlet 16, a connecting base 27 and a central pre-mixed gas passage 28. The central porous burning head 25 is disposed at a top outlet of a middle pipeline of the annular central porous burner 14. The purified air inlet 16 is formed in the bottom of the annular central porous burner 14 and is communicated with the purified air annular passage, and the annular central porous burner 14 is fixed to the base 27 connected with the atomizer. The burned mixture (hydrogen-oxygen mixture+atomized water samples) rises to the top outlet from the central pre-mixed gas passage 28 of an annular structure along a pipeline, flows out of 25 small holes having a diameter of 1 mm which are uniformly distributed in three rows in the central porous burning head 25, and is ignited.

Design parameters of the annular central porous burner 14 may be preferably designed as follows:

the purified air annular passage 26: φ32×20, H100;
the pre-mixed gas passage 28: φ20×16, H56.5;
the central porous burning head 25: φ20, δ3; 25×φ1.0 small holes which are uniformly distributed in three rows (8+9+8); and
the pressure of the purified air inlet 16: 0.2 MP, flow: 3 L/min.

Specifically, the purified air is air obtained by removing solid and liquid particles from the air outputted by an air oil-less compressor 68 through 0.1μ of precision filter 70. The "purified air" enters the purified air annular passage 26 from the purified air inlet 16 in the bottom of the annular central porous burner 14. The pressure of the purified air is higher than the pressure of the burned mixture. A micropositive pressure annular protective cover is formed around a flame torch emitting an emission spectrum of measured elements and formed above the burner. The purified air annular protective cover has the function of automatically diffusing air towards the periphery of the flame. Various trace analysis interference elements (salt mist and dust particles) in a surrounding space environment may be effectively prevented from entering an atomized inner cone, thereby achieving the aims of performing trace analysis under general laboratory environment conditions and obtaining a stable measurement result.

In a preferred solution, the flame atomization system II further includes: a condensing reflector 17 and an incident condenser 18. The incident condenser 18 faces a inner cone 15. A φ30 refined coating concave condensing reflector 17 is vertically placed behind the inner cone 15. Reflected light formed by reflection of the concave condensing reflector 17 and a spectral signal emitted by the inner cone 15 are superposed together to enter the incident condenser 18. The incident condenser 18 faces the center of an incident slit 29 of an automatic scanning second-order differential precision grating monochromator 33. A flame emission spectrum focused by the incident condenser 18 enters a plane mirror 36 of the automatic scanning second-order differential precision grating monochromator 33 from the incident slit 29. The function of the condensing reflector 17 is as follows: spectral emission intensity of sodium entering the incident slit 29 of the automatic scanning second-order differential precision grating monochromator 33 is enhanced by about 50%, thereby increasing overall sensitivity of trace sodium measurement.

Embodiment 4

Figure 5:
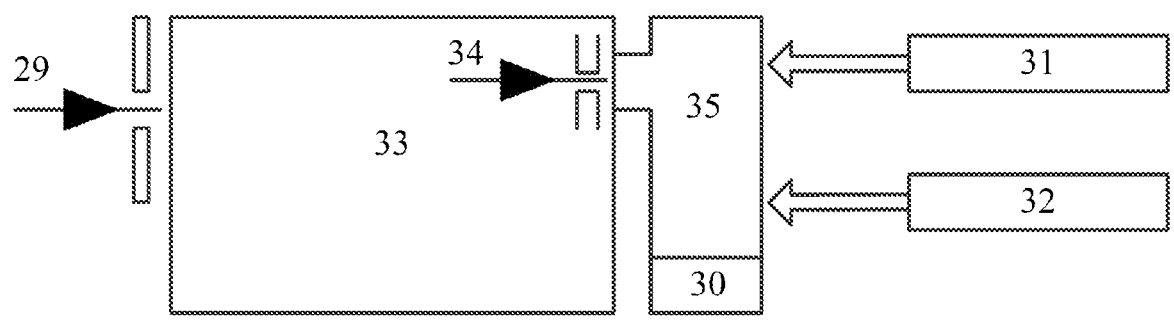
FIG. 5 is a structural schematic diagram of a photoelectric sensor system provided in a preferred embodiment of the present disclosure.

By referring to FIG. 5 and FIG. 9, a photoelectric sensor system provided in an embodiment of the present disclosure includes a photomultiplier 35, and an automatic scanning second-order differential precision grating monochromator 33, a pre-amplifier 30, a photomultiplier negative high voltage module 31 and a photomultiplier voltage bias circuit 32 which are respectively connected with the photomultiplier 35. The function of the automatic scanning second-order differential precision grating monochromator 33 is as follows: after rapid scanning of a characteristic spectrum having a wavelength of 589.0 nm from a sodium atom in an analytical sample generated by flame burning, radiated under a high temperature condition and submerged in a strong background interference spectrum, a second-order differential modulation (frequency) spectrum of the characteristic spectrum with the wavelength of 589.0 nm of the sodium atom, with a modulation frequency of 333 Hz, is outputted only. An exit slit of the automatic scanning second-order differential precision grating monochromator 33 faces an optical path entrance of the photomultiplier 35 and irradiates a cathode of the photomultiplier. The photomultiplier 35 receives second-order differential modulation spectrum excitation having the wavelength of 589.0 nm of the sodium element, and generated second-order differential frequency-modulated current is outputted to the pre-amplifier 30.

Figure 6:
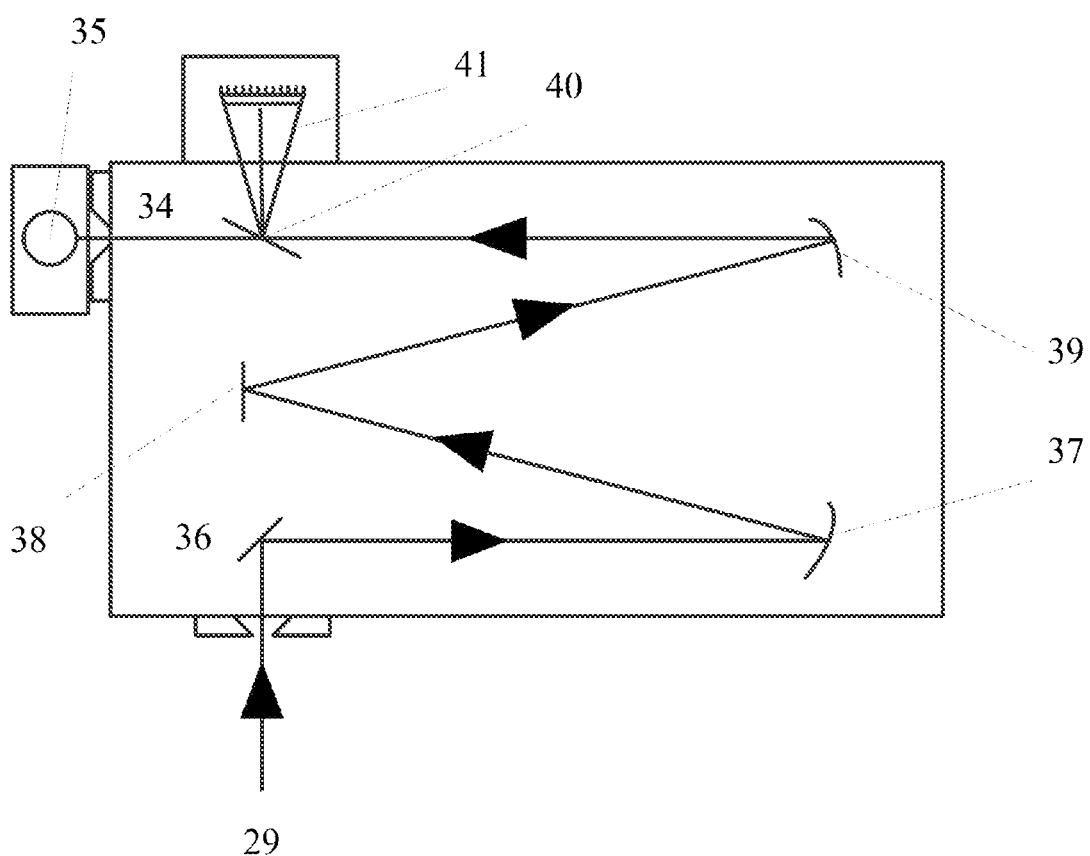
FIG. 6 is an optical path diagram of an automatic scanning second-order differential precision grating monochromator provided in a preferred embodiment of the present disclosure.

By referring to FIG. 5, FIG. 6 and FIG. 9, the automatic scanning second-order differential precision grating monochromator 33 includes the incident slit 29 and the exit slit 34 of fixed width and height, a plane mirror 36, a collimating mirror 37, an automatic scanning precision grating 38, a focusing objective, a wavelength modulation plane mirror 40 and a low-frequency oscillator drive coil 41. The incident slit 29 is a "scribed line" having a fixed width 0.1 mm and carved on a refined coating glass surface. The scribed line having the fixed width 0.1 mm is vertically installed. The "scribed line" having the fixed width 0.1 mm means that a height of the incident slit is 10 mm. The exit slit 34 faces an optical path entrance of the photomultiplier 35. The exit slit 34 is also a vertically installed scribed line having a fixed width 0.1 mm and carved on the refined coating glass surface. The automatic scanning precision grating 38 has a wavelength range of 587-591 nm, a used wavelength of 589.0 nm, and a blaze wavelength of 500 nm. A number of grating lines is 1200 g/mm, and a focal length is 320 mm.

The flame emission spectrum entering the automatic scanning second-order differential precision grating monochromator 33 from the incident slit 29 is a composite spectrum including a continuous spectrum emitted by high-temperature flame particles and a molecular radiation band spectrum emitted by molecular substances (i.e., a characteristic spectrum of 589.0 nm of sodium and "background interference" spectral lines adjacent to a characteristic line wavelength). The composite spectrum directly irradiates the plane mirror 36 after entering. The plane mirror 36 is disposed on a focal plane of the collimating mirror 37 and reflects the incident light onto a mirror surface of the collimating mirror 37. The collimating mirror 37 is an off-axis parabolic mirror. The automatic scanning precision grating 38 is disposed on an optical path of parallel reflected light of the collimating mirror 37. By virtue of diffraction of the automatic scanning precision grating 38, the incident composite spectrum is decomposed into set monochromatic light of sodium, that is, a characteristic spectrum of 589.0 nm of sodium. The beam of monochromatic light is emitted in parallel into the focusing objective 39 disposed on an optical path of the monochromatic light outputted from the automatic scanning precision grating 38. The wavelength modulation plane mirror 40 is disposed on the optical path of the reflected light of the focusing objective 39 and fixed to a vibrating diaphragm of a low frequency oscillator. The vibrating diaphragm of the low frequency oscillator is driven by the low-frequency oscillator drive coil 41 to perform rapid scanning. The low-frequency oscillator drive coil 41 is connected with an output end of a wavelength modulation power amplifier 67 of a micro-current phase-locked amplifier 54. A lagging edge of a symmetrical square wave at a frequency of 333 Hz generated by a pulse generator 60 from the micro-current phase-locked amplifier 54 is processed by a ½ frequency divider 65 and an integrator 66 to generate a triangular wave excitation at a frequency of 166.5 Hz, and the vibrating diaphragm is driven to drive the plane mirror 40 to make a rapid periodic motion, so that the characteristic spectrum (monochromatic light) having the wavelength of 589.0 nm of the sodium element from the focusing objective 39 and the "background interference" spectral lines adjacent to the characteristic spectrum are rapidly scanned on the left and right of the exit slit 34. Because changes of the (background interference) spectral lines of the continuous spectrum emitted by the high-temperature flame particles and the molecular radiation band spectrum emitted by the molecular substances in the aspect of the wavelength are relatively wide and gentle, these "background interference" spectral lines are "flattened" and then disappear after performing second-order differential processing on a wavelength. In this way, after wavelength scanning of a wavelength modulation component, only the second-order differential frequency-modulated spectrum of the characteristic spectrum having the wavelength of 589.0 nm of the sodium element, with a modulation frequency of 333 Hz, is outputted only from the exit slit 34 of the second-order differential precision grating monochromator (the plane mirror on the vibrating diaphragm of the oscillator completes a reciprocating motion, and emergent rays are scanned twice at the exit slit, so the modulation frequency of an emergent characteristic spectrum is 333 Hz, i.e., a scanning cycle is 3 ms). Meanwhile, the (background interference) spectral lines of the continuous spectrum emitted by the high-temperature flame particles and the molecular radiation band spectrum emitted by the molecular substances are automatically eliminated. After the background interference is eliminated, the second-order differential modulated (frequency-modulated) spectrum faces the optical path entrance of the photomultiplier 35 via the exit slit 34 and is irradiated on the cathode of the photomultiplier 35.

The photomultiplier 35 may be a CR131 side window type photomultiplier, and has a diameter of 28 mm, a spectral response range of 200-800 nm and a peak wavelength of 400 nm. Quantum efficiency of the sodium spectrum of 589.0 nm reaches about 95%, and dark current of the anode is less than 5 nA. The photomultiplier voltage bias circuit 32 may adopt a resistor voltage dividing type power supply circuit. The circuit forms a resistance-chain voltage divider by virtue of 11 resistors, and respectively provides stable direct-current voltage for 10-stage dynodes. The anode of the photomultiplier 35 is connected with power ground of the photomultiplier negative high voltage module 31 by virtue of a high-resistance resistor R11 (2 MΩ). Weak second-order differential frequency-modulated current outputted from the anode is subjected to I-V conversion via the R11 into a "second-order differential frequency-modulated voltage" signal. The weak frequency-modulated voltage signal is directly connected to a first-stage in-phase input end of the pre-amplifier 30 by virtue of a section of screened feeder of about 2 cm long. A negative high voltage outputted from the photomultiplier negative high voltage module 31 is connected to the cathode of the photomultiplier 35. The anode of the photomultiplier 35 is tightly connected with an input end of the pre-amplifier 30 of the micro-current phase-locked amplifier 54.

When the second-order differential modulated spectrum is irradiated on the cathode of the photomultiplier 35, a photocathode excites photoelectrons into vacuum (primary excitation), and the excited photoelectrons are modulated by the same frequency. These frequency-modulated photoelectrons enter a dynode system of the photomultiplier 35 under the effect of an electric field of a focusing electrode. Electrons (secondary excitation) excited on a multiplier electrode (dynode) are accelerated by an electric field of a next-stage multiplier electrode, fly to the electrode and impact the electrode to excite more electrons again, thereby realizing multiplier amplification by virtue of step-by-step secondary electron emission. The amplified frequency-modulated electrons are collected by the anode of the photomultiplier 35 to serve as a (frequency-modulated photocurrent) signal and are outputted.

A weak photoelectric signal outputted from the photomultiplier 35 generally has an amplitude of a few millivolts (or lower) only. Direct transmission of the weak electric signal is easily "submerged" by interference of external electrical noise. Therefore, in embodiments of the present disclosure, the "second-order differential frequency-modulated voltage" signal from the photomultiplier is pre-amplified by using the pre-amplifier 30 having high input impedance, and in circuit design, the pre-amplifier 30 is designed into a small annular circuit board and the annular circuit board is directly fixed to a holder of the photomultiplier. The pre-amplifier 30 is a low-noise voltage amplifier which is embedded into a shielding housing of the photoelectric sensor system and composed of two-stage high-performance operational amplifiers µA741. A working power supply is 12V and is respectively supplied from a ±12V output terminal of a power module. An output port is directly connected to an input port of a main signal amplifier 58 of the micro-current phase-locked amplifier 54.

Figure 7:
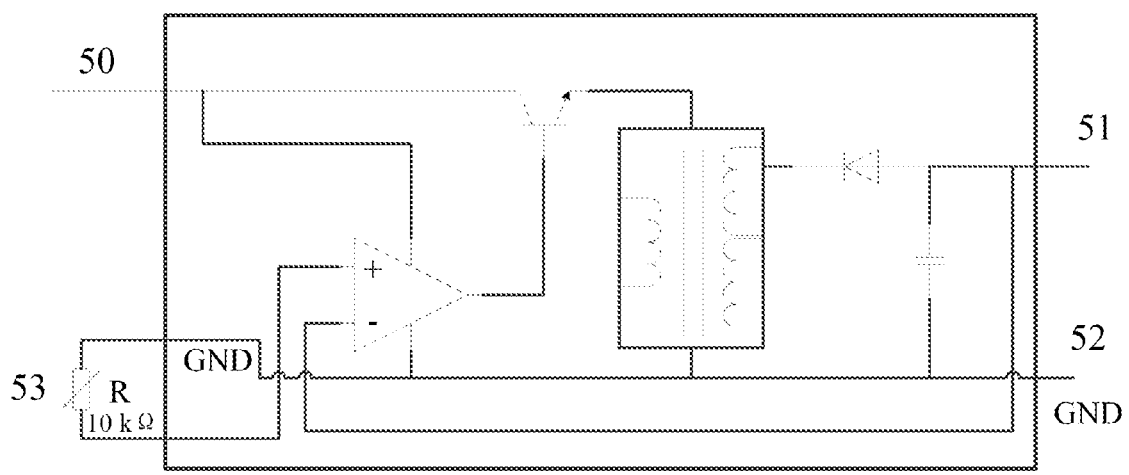
FIG. 7 is a control principle diagram of a negative high voltage module provided in a preferred embodiment of the present disclosure.
Figure 7:
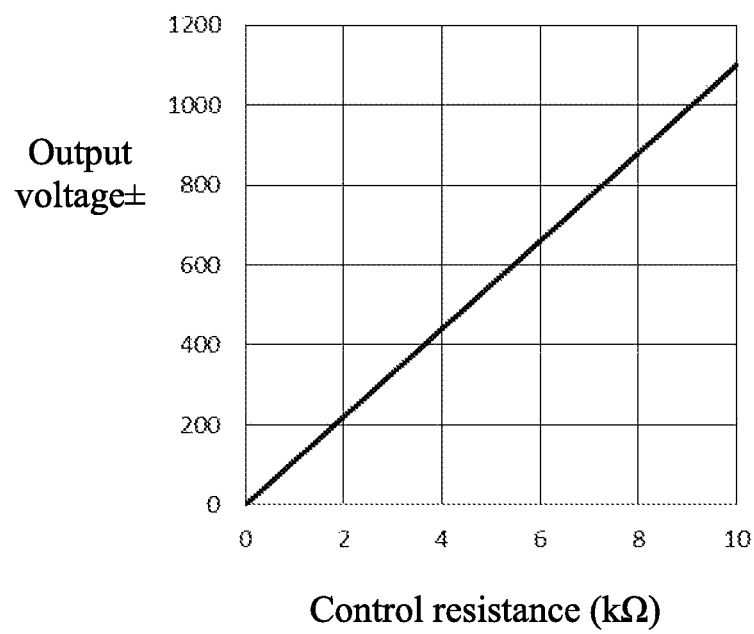

The "second-order differential frequency-modulated current (nA level)" generated by excitation of the "second-order differential modulated (frequency-modulated) spectrum" having the wavelength 589.0 nm of the sodium element and outputted by the photomultiplier 35 is subjected to I-V conversion by virtue of a high-resistance resistor R11 (2 MΩ) bridged to the anode of the photomultiplier 35 and the power ground of the negative high voltage module 31, and a weak "second-order differential frequency-modulated current" signal from the anode of the photomultiplier 35 is converted into a "second-order differential frequency-modulated voltage" signal. The weak frequency-modulated voltage signal is directly connected to the first-stage in-phase input end (IN) of the pre-amplifier 30 by virtue of the section of the screened feeder of about 2 cm long. A weak signal outputted from the anode of the photomultiplier 35 is amplified by 600 times by the pre-amplifier 30 to obtain the "second-order differential frequency-modulated voltage" signal. A direct-current analog signal outputted from a low pass filter 64 of the micro-current phase-locked amplifier 54 is transmitted to a built-in 24-bit missed-code-free low-power-consumption (4 mW) Δ–Σ analog/digital (A/D) converter in a single-chip MSC1210Y5 of a data acquirer 55 and converted into a digital signal. As shown in FIG. 7, the negative high voltage module 31 is a special power supply for supplying power to the photomultiplier. In order to ensure stability of a signal outputted by the photomultiplier and lower a noise level of the photomultiplier as much as possible, the negative high voltage module selected in the present disclosure outputs high direct-current voltage 51 having a ripple factor less than 0.005% and a maximum drift less than +0.03%/h. The negative high voltage module used in the present disclosure has an input voltage 50 of +12V and an output voltage 51 of 0-1100V. The high voltage at the output end is changed by changing the resistance at an adjusting end of the high voltage module, and the resistance is adjusted by a 10 kΩ potentiometer. A control principle of the output voltage is regulated by a regulation control resistor 53. The regulation control resistor 53 is a 10 kΩ precision digital potentiometer. The negative high voltage of the photomultiplier is regulated by controlling a programming digital potentiometer through an upper embedded industrial computer. The precision digital potentiometer 53 adopts an X9C103 non-volatile digital potentiometer in American XICOR Company.

The high-voltage direct-current output voltage 51 of the negative high voltage module 31 is connected with the cathode of the photomultiplier by virtue of a shielded cable. An outer shielding layer of the shielded cable of the photoelectric sensor system shall be connected with a common ground terminal of the negative high voltage module, a ground terminal (negative high voltage power ground of the photomultiplier) of an anode jumper loading resistor R11 of the photomultiplier 35, a common ground terminal 49 of the pre-amplifier and "ground" of a drive coil 41 of the low frequency oscillator (i.e., common ground GND of the micro-current phase-locked amplifier 54) together. In order to reduce influence and interference of power-frequency stray noise current, a shell of the automatic scanning second-order differential precision grating monochromator 33 shall be properly connected with the "ground" of the drive coil 41 of the low frequency oscillator.

The photomultiplier 35, a signal feeder, the negative high voltage module 31, the pre-amplifier 30 and the photomultiplier voltage bias circuit 32 are shielded by a metal shielding housing to form the photoelectric sensor system. Interference of a space stray electromagnetic field caused by power frequency current from an industrial power supply may be reduced to a minimum degree, and a noise level of a high-frequency irregular pulse interference signal generated when detecting a weak light signal by the photomultiplier may be lowered to the greatest degree.

Embodiment 5

Figure 8:
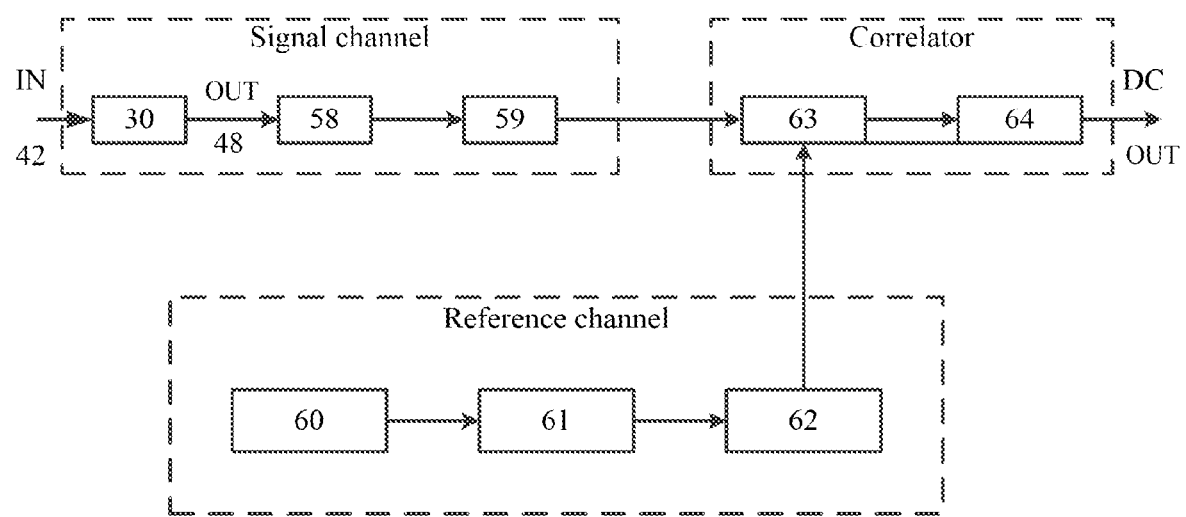
FIG. 8 is a structural schematic diagram of a microcurrent phase-locked amplifier provided in a preferred embodiment of the present disclosure.

By referring to FIG. 8 and FIG. 9, a data acquisition system provided in an embodiment of the present disclosure includes a micro-current phase-locked amplifier 54 and a data acquirer 55.

The micro-current phase-locked amplifier 54 and a pre-amplifier 30 form a signal conditioning module. The micro-current phase-locked amplifier 54 is composed of three parts: a signal channel (including the pre-amplifier 30, a main amplifier 58 and a band-pass filter 59), a reference channel (including a pulse generator 60, a phase-locked loop 61 and a phase shifter 62), and a correlator (including a phase-sensitive detector 63 and a low pass filter 64).

The signal channel has effects of amplifying a frequency-modulated input signal accompanied by noise to a level enough to push the correlator to work, and performing preliminary removal on noise beyond a signal passband by virtue of a filtering function of a specially matched band-pass filter, so as to widen a dynamic range of phase-sensitive detection. The reference channel has an effect of providing a square wave having the same frequency as an input signal. The correlator is an electronic circuit for completing a cross-correlation function operation between a detected signal and a reference signal, thereby realizing conversion of the frequency from alternating current to direct current.

The pre-amplifier 30 is a low noise amplifier embedded into the shielding housing of the photoelectric sensor system (FIG. 5 and FIG. 8). The pre-amplifier 30 outputs a "second-order differential frequency-modulated voltage" signal obtained by amplifying a weak signal outputted from the anode of the photomultiplier by 600 times. An output port (OUT) of the pre-amplifier is directly connected to an input port of a main signal amplifier 58 of the micro-current phase-locked amplifier 54 of the signal conditioning module.

The main signal amplifier 58 is a voltage amplifier composed of high-performance operational amplifiers µA741 and capable of precisely amplifying the "second-order differential frequency-modulated voltage" signal outputted by the pre-amplifier 30. A designed voltage gain is 20 times.

The band-pass filter 59 has a pass-band width of 100 HZ-400 HZ, and is capable of effectively blocking power frequency (50 HZ) noise and high-frequency irregular pulsed (thermal) noise generated by the photomultiplier.

The reference channel of the micro-current phase-locked amplifier 54 includes three parts: the pulse generator 60, the phase-locked loop 61 and the phase shifter 62.

The pulse generator 60 is a "duty ratio adjustable square wave signal generator" composed of a 555 time base integrated circuit and having a generation cycle of 3 ms and a duty ratio of ½.

The phase-locked loop 61 is a closed loop tracking system, and has a function of tracking a phase and a frequency of the input signal. The phase-locked loop is a circuit which is synchronous on the frequency and the phase using an output signal (a square wave reference signal generated by an oscillator) and the input signal. In a synchronization (generally called locked) status, a phase difference between the output signal and the input signal of the oscillator is zero.

In the circuit design of the phase-locked amplifier in the present disclosure, a lagging edge of a symmetrical square wave having a frequency of 333 Hz (a cycle of 3 ms) generated by the pulse generator 60 is transmitted to a ½ frequency divider 65 and an integrator 66 and processed so as to generate a triangular wave having a frequency of 166.5 Hz (a cycle of 6 ms). After the triangular wave signal having the frequency of 166.5 Hz is transmitted to a power amplifier 67 and is amplified, a drive coil 41 of a low frequency oscillator inside an automatic scanning second-order differential precision grating monochromator 33 is directly driven to drive a vibrating diaphragm of the low frequency oscillator, so as to drive a plane mirror 40 to make a rapid cyclic motion (the plane mirror on the vibrating diaphragm of the oscillator completes a reciprocating motion, and emergent rays are scanned twice at the exit slit, so the modulation frequency of an emergent characteristic spectrum is 333 Hz, i.e., a scanning cycle is 3 ms), thereby realizing rapid scanning of incident light (characteristic spectrum monochromatic light) and generating and outputting a "second-order differential modulated (frequency-modulated) spectrum" of a wavelength 589.0 nm of the sodium element. This design processing ensures that the modulation frequency of the "second-order differential modulated (frequency-modulated) spectrum" of the wavelength 589.0 nm of the sodium element is the same as the frequency of the square wave signal generated by the pulse generator 60 of the reference channel of the phase-locked amplifier (333 Hz). A leading edge of the square wave reference signal generated by the pulse generator 60 forms a square wave having a duty ratio of 1/1 by the phase-locked loop 61 composed of a 555 time base integrated circuit, and the square wave is added into the phase shifter 62 so that the reference signal and the input signal have consistent phases.

The phase shifter 62 has a function of changing a phase of a waveform outputted by the reference channel so that the phase is adjustable within 360°.

The correlator is composed of two function modules: the phase sensitive detector (PSD) 63 and the low pass filter 64. The "second-order differential frequency-modulated voltage signal" of a characteristic spectrum of an output port of the pre-amplifier 30 from the micro-current phase-locked amplifier 54 passes through the main signal amplifier 58 of the signal channel (an amplification factor is about 20 times) and the band-pass filter 59, and then enters the phase sensitive detector (demodulator) 63 of the correlator and is demodulated and further amplified (an amplification factor is about 5 times). A high-frequency noise level such as a "sum frequency component" generated by the phase sensitive detector is further filtered from a direct-current analog signal outputted from the phase sensitive detector (demodulator) 63 and forming direct proportion to a sodium concentration in a water sample by virtue of the low pass filter 64 which is connected in series. An input signal having the same frequency as the reference signal is converted into the direct-current analog signal. The direct-current analog signal is a direct-current analog signal which is obtained by second-order differential operation processing without any background interference and which is kept a good linear relation with a $Na^+$ concentration in the water sample. The direct-current analog signal is transmitted to a built-in 24-bit missed-code-free low-power-consumption (4 mW) $\Delta$-$\Sigma$ analog/digital (A/D) converter in a single-chip MSC1210Y5 of the data acquirer 55 and is converted into a digital signal.

The data acquirer 55 is responsible for acquiring analog data from a sensor and responding to an instruction transmitted by the embedded industrial computer 56. The outputted digital signal is transmitted to the embedded industrial computer 56, and the embedded industrial computer 56 performs data storage and processing, performs control regulation for the operation of an instrument, and realizes network transmission of the data and other functions. The data acquirer 55 may adopt a data acquirer taking the single-chip MSC1210Y5 as a core. The single-chip MSC1210Y5 is provided with an 8-path 24-bit analog-digital converter, and is composed of an input multiplexer, a programmable gain amplifier, a regulator, a digital filter, a reference voltage stabilizing source and the like.

Embodiment 6

Figure 10:
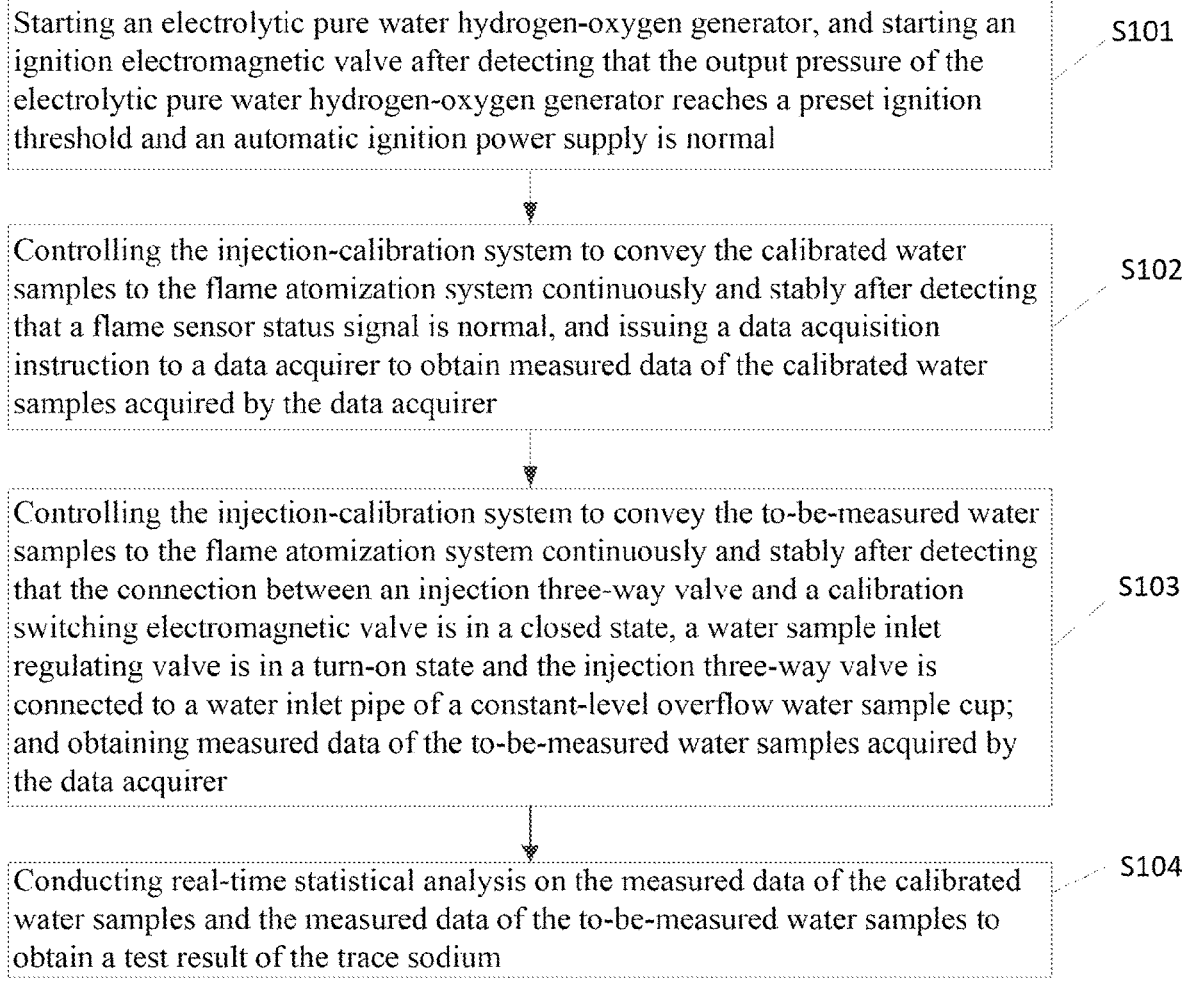
FIG. 10 is a flow chart of an online monitoring method provided in a preferred embodiment of the present disclosure.

By referring to FIG. 10, an online monitoring method for trace sodium in high-purity water provided in an embodiment of the present disclosure is applied to an embedded industrial computer and includes the following steps:

S101: an ignition step: starting an electrolytic pure water hydrogen-oxygen generator, and starting an ignition electromagnetic valve after detecting that the output pressure of the electrolytic pure water hydrogen-oxygen generator reaches a preset ignition threshold and an automatic ignition power supply is normal.

It should be noted that, the method further includes a system setting step. The step is preferably performed before the method, and specifically includes: setting a characteristic spectrum wavelength of an automatic scanning second-order differential precision grating monochromator as 589.0 nm; setting a ripple factor of a high direct-current voltage outputted by a negative high voltage module of the photomultiplier to be less than 0.005% and setting a maximum drift to be less than ±0.03%/h.

From an operational level, after a user turns on a host power supply, a monochromator power supply, a silicon nitride ignition power supply, an industrial personal computer motherboard and a touch screen power supply, an industrial personal computer is connected with a lower computer (a host) by using a USB connecting cable, and the industrial personal computer is connected with the monochromator by using a USB connecting cable. An icon of online monitoring software of the trace sodium is started, and the system setting step is completed in a man-machine interface dialog box of the software. Parameters of the system setting include but not limited to system time setting, characteristic spectrum wavelength setting of 589.0 nm, negative high voltage setting of a photomultiplier, and user name setting. After the setting is completed, the embedded industrial computer performs system detection, and detection parameters include but not limited to the output pressure of an electrolytic hydrogen-oxygen generator, a flame sensor status signal, an on-off state of a silicon nitride automatic ignition power supply, an output pressure signal of air compressor, a calibration status signal, a status signal of a calibration switching valve 3, a status signal of an injection three-way valve 4, a status signal of a water sample inlet regulating valve 10, and the like. When the output pressure of the electrolytic pure water hydrogen-oxygen generator is detected to reach a preset ignition threshold (0.15 MP), the silicon nitride automatic ignition power supply (24 VDC) is normal, i.e., an ignition program may be started.

S102: a calibration step: controlling the injection-calibration system to convey the calibrated water samples to the flame atomization system continuously and stably after detecting that a flame sensor status signal is normal, and issuing a data acquisition instruction to a data acquirer to obtain measured data of the calibrated water samples acquired by the data acquirer.

Figure 11:
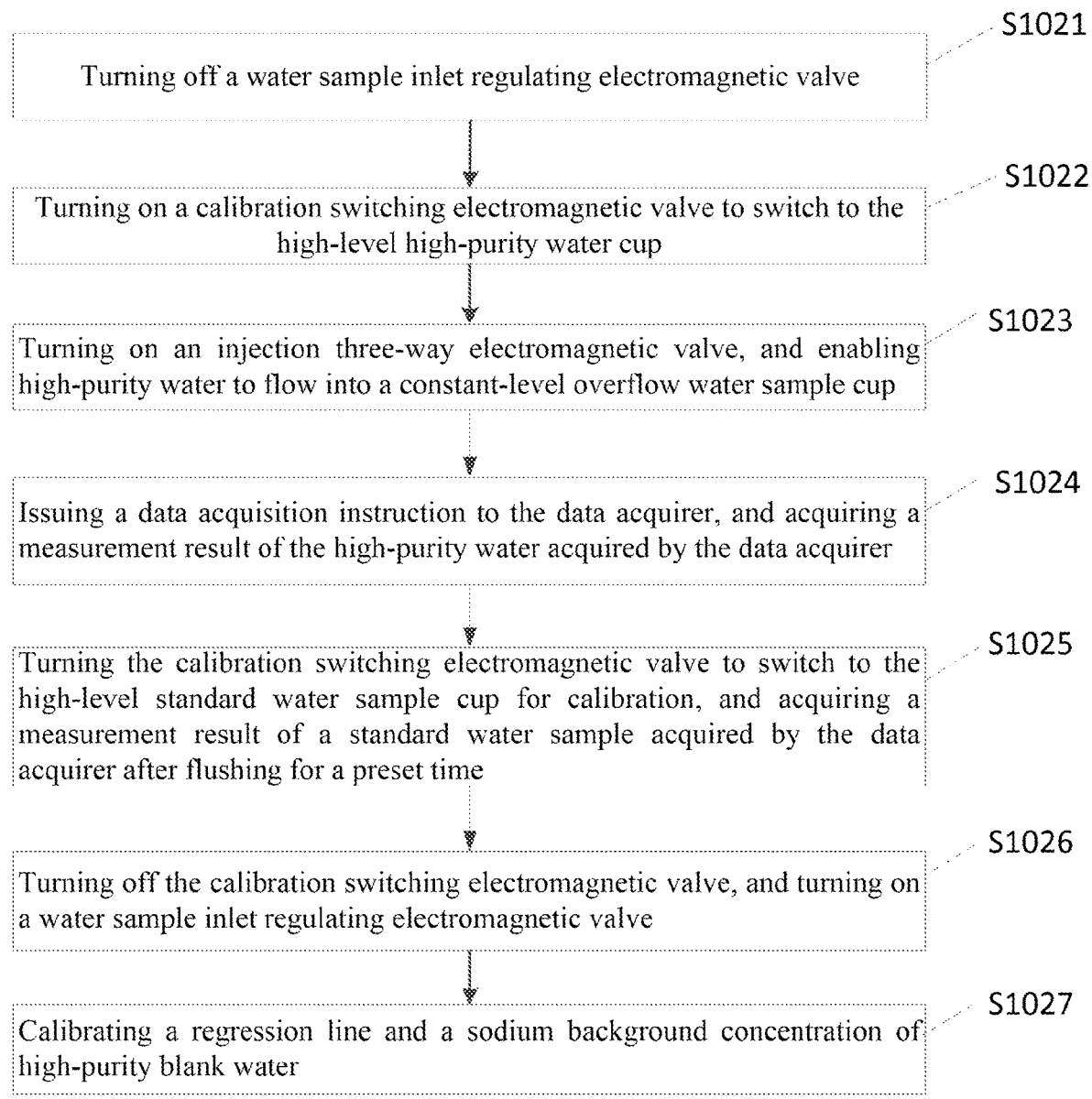
FIG. 11 is a flow chart of a calibration method provided in a preferred embodiment of the present disclosure.

It should be noted that, before the calibration step, a high-level high-purity water cup for calibration 1 and a high-level standard water sample cup for calibration 2 shall be respectively filled with high-purity water and 10 μg/L of sodium standard water samples. By referring to FIG. 11, the calibration step S102 specifically includes:

S1021, turning off a water sample inlet regulating electromagnetic valve.

S1022, turning on a calibration switching electromagnetic valve to switch to the high-level high-purity water cup.

S1023, turning on an injection three-way electromagnetic valve, and enabling high-purity water to flow into a constant-level overflow water sample cup.

Specifically, after the injection three-way electromagnetic valve is turned on, the high-purity water enters a water inlet pipe of the constant-level overflow water sample cup to flow into the constant-level overflow water sample cup, and a water sample from the high-level high-purity water cup is automatically drawn into an atomizing chamber via an injection capillary pipe to complete the processes of atomization, mixing and droplet separation, and is ignited above an outlet of a central porous burning head of an annular central porous burner to form a flame which radiates a sodium spectrum of 589.0 nm.

S1024, issuing a data acquisition instruction to the data acquirer, and acquiring a measurement result of the high-purity water acquired by the data acquirer.

Specifically, the embedded industrial computer issues an acquisition instruction to a single-chip of the data acquirer. The single-chip acquires a direct-current analog signal from a low pass filter of a micro-current phase-locked amplifier, and the direct-current analog signal is converted into a digital signal by an A/D converter and is transmitted to the embedded industrial computer for storage and further processing.

S1025, turning the calibration switching electromagnetic valve to switch to the high-level standard water sample cup for calibration, and acquiring a measurement result of a standard water sample acquired by the data acquirer after flushing for a preset time.

Specifically, after injection reading of the high-purity water is completed, the calibration switching electromagnetic valve is switched to the high-level standard water sample cup for calibration; a 10 μg/L of sodium standard water sample flows into the constant-level overflow water sample cup; and the data is acquired after flushing for several minutes, thereby completing data acquisition of the 10 μg/L of sodium standard water sample.

S1026, turning off the calibration switching electromagnetic valve, and turning on a water sample inlet regulating electromagnetic valve.

S1027, calibrating a regression line and a sodium background concentration of high-purity blank water.

Figure 12:
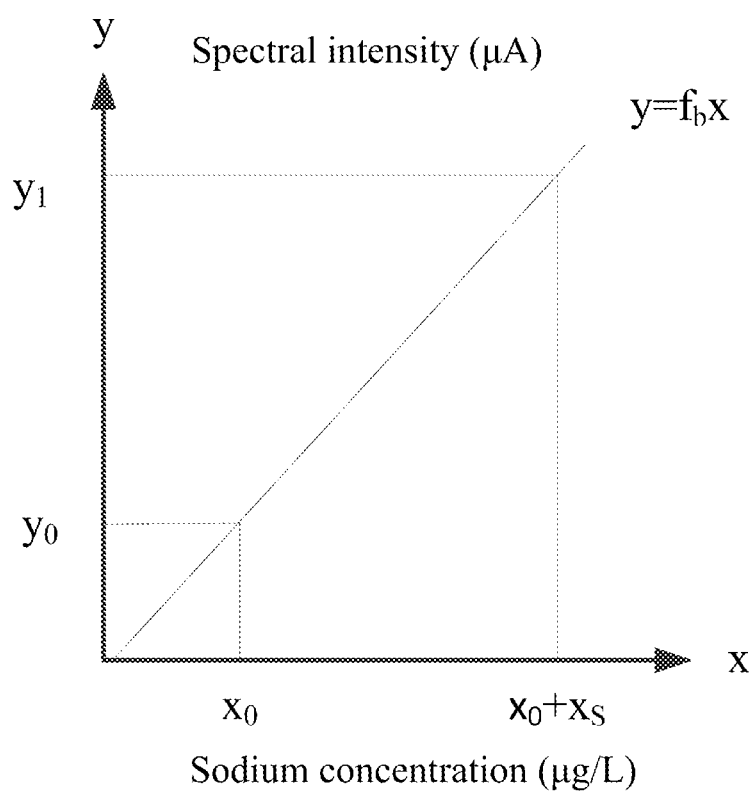
FIG. 12 is a Lomakin relation curve of atomic emission spectroscopy provided in a preferred embodiment of the present disclosure.

Specifically, the sodium ion in the sample is atomized in a high-temperature flame and excited to radiate a "characteristic spectrum" of the sodium atom. Under the condition that the sodium concentration is extremely low (trace), the intensity of the spectral line is in direct proportion to the sodium ion concentration in the sample, as indicated by Lomakin formula (as shown in FIG. 12).

The Lomakin formula has physical significances as follows: a calibration curve of atomic emission spectroscopy is certainly a straight line passing through an origin (when and only when the sodium ion concentration in the water sample is zero, a measured value of the spectral line intensity may be zero), which provides a theoretical basis without preparing "sodium-free water" for measurement calibration of the atomic emission spectroscopy. In fact, under the conditions of the prior art, actual "sodium-free water" does not exist.

Namely:

$$y = f_b x \tag{1}$$

$$x = y/f_b \tag{2}$$

In the formula, x represents a real concentration (μg/L) of sodium in the water sample;

y represents a spectral line intensity value (reading μA of a spectral line intensity scale of the instrument)

$f_b$ represents a slope of the regression line.

Setting that.

0# water sample as high-purity blank water;

A sodium background concentration $x_0$ of the high-purity blank water is set as $C_0$ (μg/L);

A spectral line intensity value $y_0$ of the blank water is measured;

Then, $y_0 = f_b x_0$ \hfill (3)

1# water sample is set as a standard solution obtained by adding sodium content $x_S$ into a high-purity blank water sample;

The sodium concentration of the 1# water sample is set as $x_1$ (μg/L), and the spectral line intensity value y1 is measured;

Then, $y_1 = f_b x_1$ \hfill (4)

$x_1 = x_0 + x_S$ (an actual sodium concentration of the 1# water sample) \hfill (5)

The formula (5) is substituted into the formula (4) to obtain:

$$f_b = \frac{y_1}{x_0 + x_S} \tag{6}$$

The formula (6) is substituted into the formula (3) to obtain the sodium background concentration of the high-purity blank water;

$$x_0(C_0) = \frac{y_0 x_S}{y_1 - y_0} \quad (7)$$

The formula (7) is substituted into the formula (6) to solve the slope:

$$f_b = \frac{y_1 - y_0}{x_S} \quad (8)$$

The formula (8) is substituted into the Lomakin-Scherbe formula (1)
A calculation formula of the actual sodium concentration in the water sample is obtained:

$$x = \frac{y}{f_b} = \frac{x_S}{y_1 - y_0} y \quad (9)$$

In the present embodiment, the calibration result is automatically calculated, and a regression straight line diagram (that is, a Lomakin relation curve) of the sodium background concentration value C0 [μg/L] of the high-purity blank water and the calibration result is automatically given. It will be seen from the above deduction process that, when the trace sodium is measured by adopting a "two-point calibration method" provided by this instrument, a "precondition" of the "sodium-free water" is not required. The actual trace sodium content in the water sample may be accurately determined as long as water on the same level as that of the sodium content in the sample is taken as "blank" water.

S103: a measurement step: controlling the injection-calibration system to convey the to-be-measured water samples to the flame atomization system continuously and stably after detecting that the connection between an injection three-way valve and a calibration switching electromagnetic valve is in a closed state, a water sample inlet regulating valve is in a turn-on state and the injection three-way valve is connected to a water inlet pipe of a constant-level overflow water sample cup; and obtaining measured data of the to-be-measured water samples acquired by the data acquirer.

Specifically, after the calibration step is completed, the method automatically transfers to a measurement step, and measurement of a real-time actual sodium concentration of an online water sample is started according to an instruction of a measurement procedure. At this moment, connection between the injection three-way valve and the calibration switching electromagnetic valve is in a closed state; the water sample inlet regulating valve is in a turn-on state; and the injection three-way valve is connected to the water inlet pipe of the constant-level overflow water sample cup. The water samples from the water sample inlet regulating valve of a boiler water-steam sampling rack continuously flow through the constant-level overflow water sample cup. A measuring frequency is preferably 1 time per 10 min (a real-time water sample measurement is completed by performing a reading operation every 10 minutes). When the acquisition of measured data is triggered, the industrial personal computer commands the single-chip to turn off the water sample inlet regulating valve. After data acquisition is completed, the water sample inlet regulating valve is immediately automatically turned on. Thus, with the adoption of programmed analytical operations of continuous injection and intermittent static measurement, the injection valve is turned off by a computer program in the measuring process to realize static measurement of the constant-level overflow water sample cup, thereby ensuring real-time representativeness of the measurement result, stability of the measurement condition and repeatability of the measurement result.

S104: a data processing step: conducting real-time statistical analysis on the measured data of the calibrated water samples and the measured data of the to-be-measured water samples to obtain a test result of the trace sodium.

Specifically, each measured data outputted is an arithmetic mean value of statistic values of 6 times of parallel measured data at an interval of 1 second. Meanwhile, standard deviation and relative standard deviation of the measurement result, "uncertainty" of the measurement result and other statistical data may be automatically given. The measurement result may be intelligently calibrated and directly displayed on a field LCD screen by virtue of a working curve which passes through the coordinate origin about determination of the real-time actual sodium concentration of the water sample. The calibrated measurement result is an actual content value of the sodium in the water sample.

Embodiment 7

Figure 13:
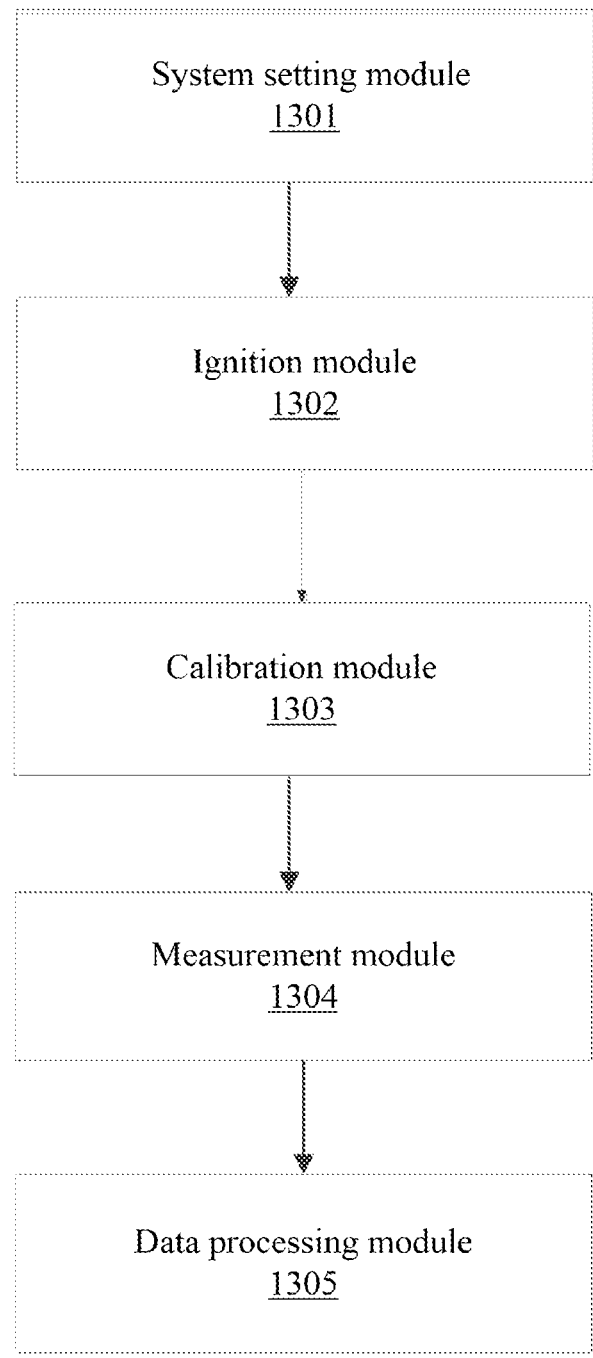
FIG. 13 is a module structural diagram of a calibration device provided in a preferred embodiment of the present disclosure.

By referring to FIG. 13, an online monitoring device for trace sodium in high-purity water provided in an embodiment of the present disclosure is applied to an embedded industrial computer and includes a system setting module 1301, an ignition module 1302, a calibration module 1303, a measurement module 1304 and a data processing module 1305.

The system setting module 1301 is configured for setting a characteristic spectrum wavelength of an automatic scanning second-order differential precision grating monochromator as 589.0 nm, and is also configured for setting a ripple factor of a high direct-current voltage outputted by a negative high voltage module of the photomultiplier to be less than 0.005% and setting a maximum drift to be less than ±0.03%/h.

The ignition module 1302 is configured for starting an electrolytic pure water hydrogen-oxygen generator, and starting an ignition electromagnetic valve after detecting that the output pressure of the electrolytic pure water hydrogen-oxygen generator reaches a preset ignition threshold and an automatic ignition power supply is normal.

The calibration module 1303 is configured for controlling the injection-calibration system to convey the calibrated water samples to the flame atomization system continuously and stably after detecting that a flame sensor status signal is normal, and issuing a data acquisition instruction to a data acquirer to obtain measured data of the calibrated water samples acquired by the data acquirer.

The calibration module 1303 is specifically configured for filling a high-level high-purity water cup for calibration and a high-level standard water sample cup for calibration with high-purity water and standard water samples respectively; turning off the water sample inlet regulating valve; turning on a calibration switching electromagnetic valve to switch to the high-level high-purity water cup; turning on an injection three-way electromagnetic valve, and enabling high-purity water to flow into a constant-level overflow water sample cup; issuing a data acquisition instruction to the data acquirer, and acquiring a measurement result of the high-purity water acquired by the data acquirer, turning the calibration switching electromagnetic valve to switch to the high-level standard water sample cup for calibration, and acquiring a measurement result of a standard water sample acquired by the data acquirer after flushing for a preset time; and turning off the calibration switching electromagnetic valve, and turning on a water sample inlet regulating electromagnetic valve.

The measurement module 1304 is configured for controlling the injection-calibration system to convey the to-be-measured water samples to the flame atomization system continuously and stably after detecting that the connection between the injection three-way valve and the calibration switching electromagnetic valve is in a closed state, the water sample inlet regulating valve is in a turn-on state and the injection three-way valve is connected to the water inlet pipe of the constant-level overflow water sample cup; and obtaining measured data of the to-be-measured water samples acquired by the data acquirer.

Specifically, the measurement module 1304 turns off the water sample inlet regulating valve according to a preset frequency, and turns on the water sample inlet regulating valve after acquiring the measured data.

The data processing module 1305 is configured for conducting real-time statistical analysis on the measured data of the calibrated water samples and the measured data of the to-be-measured water samples to obtain a test result of the trace sodium.

The above describes the preferred embodiments of the present disclosure with reference to the drawings, and is not intended to limit the protection scope of the present disclosure. Those skilled in the art may have multiple variation solutions to realize the present disclosure, e.g., to use a feature of one embodiment to another embodiment to obtain a further embodiment, without deviating from the scope and essence of the present disclosure. Any modification, equivalent replacement and improvement made within the technical conception of the present disclosure shall be included in the protection scope of the present disclosure.

INDUSTRIAL APPLICABILITY

In the online monitor for trace sodium in high-purity water, and the monitoring method and device thereof provided by the present disclosure, elements are analyzed qualitatively and quantitatively through atomic emission spectrometry according to characteristic spectrums emitted when to-be-measured element atoms in an excited state return to a ground state; and the intensity of the characteristic spectrums of the elements is configured for quantification, thereby effectively overcoming the defects of an ion selective electrode method at the aspect of detection of the trace sodium. The present disclosure is configured for real-time, quick and accurate detection of trace sodium in high-purity water, and has low cost and high sensitivity.

We claim:

1. An online monitor for trace sodium in high-purity water, comprising an injection-calibration system, a flame atomization system, a photoelectric sensor system, a data acquisition system and an embedded industrial computer which are connected successively, wherein
    the injection-calibration system is configured for continuously and stably conveying calibrated water samples and to-be-measured water samples to an inlet of an injection capillary pipe of a glass concentric pneumatic atomizer of the flame atomization system under control of the embedded industrial computer;
    the flame atomization system is configured for forming a negative pressure field by using a high-purity hydrogen-oxygen mixture as carrier gas which enters an atomizing nozzle throat of the glass concentric pneumatic atomizer, automatically drawing the calibrated water samples and the to-be-measured water samples from the injection-calibration system into an atomizing chamber for completing atomization, mixing and droplet separation, and then igniting the water samples at a high-temperature inner cone of an annular central porous burner to form a flame which radiates a sodium spectrum of 589.0 nm;
    the photoelectric sensor system is configured for quickly scanning a characteristic spectrum of sodium, producing a second-order differential modulation sodium spectrum after removing background interferences, receiving excitation of the second-order differential modulation sodium spectrum by a photomultiplier tube, producing second-order differential frequency-modulated current, and amplifying and outputting the current to the data acquisition system;
    the data acquisition system is configured for acquiring an analog signal of the second-order differential frequency-modulated current, converting the analog signal into a digital signal and outputting the digital signal to the embedded industrial computer; and
    the embedded industrial computer is configured for conducting real-time control over the operation of the injection-calibration system, the flame atomization system, the photoelectric sensor system and the data acquisition system and analyzing and processing the acquired data in real time to obtain a test result.

2. The online monitor according to claim 1, wherein the injection-calibration system comprises a constant-level overflow water sample cup (6); a water sample inlet pipe (5) of the constant-level overflow water sample cup (6) is inserted from a top overflow port of the constant-level overflow water sample cup (6) into a bottom of the constant-level overflow water sample cup (6); an outlet of the water sample inlet pipe (5) is lower than an inlet of an atomizer injection capillary pipe (7) by a first preset height difference; and the atomizer injection capillary pipe (7) is connected from the bottom of the constant-level overflow water sample cup (6) to a water sample inlet of a glass concentric pneumatic atomizer of a flame atomization system.

3. The online monitor according to claim 2, wherein an overflow port of the constant-level overflow water sample cup (6) is a bottle opening of a standard PE narrow-mouth sampling bottle of 125 mL; and flow velocity of a water sample flowing into the constant-level overflow water sample cup (6) is designed as 60 mL/min.

4. The online monitor according to claim 2, wherein the injection-calibration system further comprises: a high-level high-purity water cup for calibration (1), a high-level standard water sample cup for calibration (2), a calibration switching valve (3), an injection three-way valve (4), a fixing groove (8), an overflow water collection cup (9) and a water sample inlet regulating valve (10) from a boiler water-steam sampling rack, wherein
    the constant-level overflow water sample cup (6) is installed in the overflow water collection cup (9) through the fixing groove (8);
    the calibration switching valve (3) is a two-position three-way electromagnetic valve; and three channels are respectively connected with the high-level high-purity water cup for calibration (1), the high-level standard water sample cup for calibration (2) and the injection three-way valve (4); and another two paths of the injection three-way valve (4) are respectively communicated with the water sample inlet regulating valve (10) and the water sample inlet pipe (5).

5. The online monitor according to claim 4, wherein each of the high-level high-purity water cup for calibration (1) and the high-level standard water sample cup for calibration (2) is a bottom-opened polyethylene container, a bottom of the polyethylene container is of a conical funnel structure, and a height difference between the bottom of the container and an inlet of the atomizer injection capillary pipe (7) is a second preset height difference.

6. The online monitor according to claim 1, wherein the flame atomization system comprises a glass concentric pneumatic atomizer (11), an atomizing chamber (13), an annular central porous burner (14) and an electrolytic pure water hydrogen-oxygen generator (23), wherein the electrolytic pure water hydrogen-oxygen generator (23) is configured for electrolyzing a solid polymer electrolyte into pure water to produce hydrogen and oxygen, and inputting the produced high-purity hydrogen-oxygen mixture into the glass concentric pneumatic atomizer (11) as carrier gas; the carrier gas enters an atomizing nozzle throat of the glass concentric pneumatic atomizer (11) to form a negative pressure field; the calibrated water samples and the to-be-measured water samples from the injection-calibration system are automatically drawn into the atomizing chamber (13) for completing atomization, mixing and droplet separation, and then outputted to the upper part of an outlet of a central porous burning head of the annular central porous burner (14) and ignited to form a flame which radiates a characteristic spectrum of 589.0 nm of sodium.

7. The online monitor according to claim 6, wherein a volume ratio of hydrogen to oxygen in the high-purity hydrogen-oxygen mixture is 2:1.

8. The online monitor according to claim 6, wherein the annular central porous burner (14) comprises a central porous burning head (25) disposed at a top outlet of a middle pipeline of the annular central porous burner, a central pre-mixed gas passage (28) a purified air inlet (16) which are disposed at the bottom of the annular central porous burner, and a purified air annular passage (26) disposed around the central porous burning head (25); the purified air annular passage (26) is communicated with the purified air inlet (16); the central porous burning head (25) is a pure-titanium circular plate which comprises at least one row of uniformly distributed small holes with the same diameter, and the burned mixture rises to the top outlet from the central pre-mixed gas passage (28) along a pipeline, flows out of the small holes of the central porous burning head (25), and is ignited.

9. The online monitor according to claim 8, wherein the central porous burning head (25) is a pure-titanium circular plate which comprises three rows of uniformly distributed small holes having a diameter of 1.0 mm.

10. The online monitor according to claim 6, wherein the flame atomization system further comprises a condensing reflector (17) and an incident condenser (18); the incident condenser (18) faces the inner cone; a φ30 refined coating concave condensing reflector (17) is vertically placed behind the inner cone; reflected light formed by reflection of the concave condensing reflector (17) and a spectral signal emitted by the inner cone (15) are superposed together to enter the incident condenser (18); the incident condenser (18) faces the center of an incident slit (29) of an automatic scanning second-order differential precision grating monochromator (33); and a flame emission spectrum focused by the incident condenser (18) enters a plane mirror (36) of the automatic scanning second-order differential precision grating monochromator (33) from the incident slit (29).

11. The online monitor according to claim 6, wherein the flame atomization system further comprises an air oil-less compressor (68) and a precision filter (70); and the air oil-less compressor (68) inputs purified air filtered by the precision filter (70) for the annular central porous burner (14).

12. The online monitor according to claim 6, wherein a dew point of the purified air inputted by the annular central porous burner (14) and filtered by the precision filter (70) is less than −50° C.

13. The online monitor according to claim 1, wherein the photoelectric sensor system comprises a photomultiplier (35), and an automatic scanning second-order differential precision grating monochromator (33), a pre-amplifier (30), a photomultiplier negative high voltage module (31) and a photomultiplier voltage bias circuit (32) which are respectively connected with the photomultiplier (35) wherein an exit slit of the automatic scanning second-order differential precision grating monochromator (33) faces an optical path entrance of the photomultiplier (35) and irradiates a cathode of the photomultiplier, the photomultiplier (35) receives second-order differential modulation spectrum excitation having a wavelength of 589.0 nm of the sodium element, and generated second-order differential frequency-modulated current is outputted to the pre-amplifier (30).

14. The online monitor according to claim 13, wherein the automatic scanning second-order differential precision grating monochromator (33) comprises the incident slit (29) and the exit slit (34) of fixed width and height, a plane mirror (36), a collimating mirror (37), an automatic scanning precision grating (38), a focusing objective (39), a wavelength modulation plane mirror (40) and a low-frequency oscillator drive coil (41), wherein a composite spectrum which enters from the incident slit (29) is incident and then directly irradiates the plane mirror (36); the plane mirror (36) is disposed on a focal plane of the collimating mirror (37) and reflects the incident light onto a mirror surface of the collimating mirror (37); the collimating mirror (37) is an off-axis parabolic mirror, the automatic scanning precision grating (38) is disposed on an optical path of parallel reflected light of the collimating mirror (37); by virtue of diffraction of the automatic scanning precision grating (38), the incident composite spectrum is decomposed into set monochromatic light of sodium; the monochromatic light is emitted in parallel into the focusing objective (39) disposed on an optical path of the monochromatic light outputted from the automatic scanning precision grating (38); the wavelength modulation plane mirror (40) is disposed on the optical path of the reflected light of the focusing objective (39) and fixed to a vibrating diaphragm of a low frequency oscillator, the vibrating diaphragm of the low frequency oscillator is driven by the low-frequency oscillator drive coil (41) to drive the wavelength modulation plane mirror (40) to perform rapid scanning motion; the incident monochromatic light from the focusing objective (39) is quickly scanned to generate and output, via the exit slit (34), a second-order differential modulation spectrum of a characteristic spectrum of sodium element having a modulation frequency of 333 Hz after removing background interferences.

15. The online monitor according to claim 1, wherein the data acquisition system comprises a micro-current phase-locked amplifier (54) and a data acquirer (55), wherein the micro-current phase-locked amplifier (54) is configured for generating a triangular wave with a frequency of 166.5 Hz in such a manner that a lagging edge of a symmetrical square wave at a frequency of 333 Hz is processed by a ½ frequency divider and an integrator, to excite and drive the vibrating diaphragm to drive the plane mirror (40) to make a rapid periodic motion; and the data acquirer (55) is configured for receiving a direct-current analog signal outputted from the micro-current phase-locked amplifier (54), converting the analog signal into a digital signal and outputting the digital signal into the embedded industrial computer.

16. A method for online monitoring trace sodium in high-purity water, implemented in the industrial computer of claim 1 and comprising the following steps:
   an ignition step: starting an electrolytic pure water hydrogen-oxygen generator, and starting an ignition electromagnetic valve after detecting that a output pressure of the electrolytic pure water hydrogen-oxygen generator reaches a preset ignition threshold and an automatic ignition power supply is normal;
   a calibration step: controlling the injection-calibration system to convey the calibrated water samples to the flame atomization system continuously and stably after detecting that a flame sensor status signal is normal, and issuing a data acquisition instruction to a data acquirer to obtain measured data of the calibrated water samples acquired by the data acquirer;
   a measurement step: controlling the injection-calibration system to convey the to-be-measured water samples to the flame atomization system continuously and stably after detecting that the connection between an injection three-way valve and a calibration switching electromagnetic valve is in a closed state, a water sample inlet regulating valve is in a turn-on state and the injection three-way valve is connected to a water inlet pipe of a constant-level overflow water sample cup; and obtaining measured data of the to-be-measured water samples acquired by the data acquirer; and
   a data processing step: conducting real-time statistical analysis on the measured data of the calibrated water samples and the measured data of the to-be-measured water samples to obtain a test result of the trace sodium.

17. A device for online monitoring trace sodium in high-purity water, executed on the industrial computer of claim 1 and comprising the following modules:
   an ignition module configured for starting an electrolytic pure water hydrogen-oxygen generator, and starting an ignition electromagnetic valve after detecting that the output pressure of the electrolytic pure water hydrogen-oxygen generator reaches a preset ignition threshold and an automatic ignition power supply is normal;
   a calibration module configured for controlling the injection-calibration system to convey the calibrated water samples to the flame atomization system continuously and stably after detecting that a flame sensor status signal is normal, and issuing a data acquisition instruction to a data acquirer to obtain measured data of the calibrated water samples acquired by the data acquirer;
   a measurement module configured for controlling the injection-calibration system to convey the to-be-measured water samples to the flame atomization system continuously and stably after detecting that the connection between an injection three-way valve and a calibration switching electromagnetic valve is in a closed state, a water sample inlet regulating valve is in a turn-on state and the injection three-way valve is connected to a water inlet pipe of a constant-level overflow water sample cup; and obtaining measured data of the to-be-measured water samples acquired by the data acquirer; and
   a data processing module configured for conducting real-time statistical analysis on the measured data of the calibrated water samples and the measured data of the to-be-measured water samples to obtain a test result of the trace sodium.

18. The device according to claim 17, wherein the calibration module is specifically configured for:
   turning off a water sample inlet regulating electromagnetic valve;
   turning on a calibration switching electromagnetic valve to switch to the high-level high-purity water cup;
   turning on an injection three-way electromagnetic valve, and enabling high-purity water to flow into a constant-level overflow water sample cup;
   issuing a data acquisition instruction to the data acquirer, and acquiring a measurement result of the high-purity water acquired by the data acquirer;
   turning the calibration switching electromagnetic valve to switch to the high-level standard water sample cup for calibration, and acquiring a measurement result of a standard water sample acquired by the data acquirer after flushing for a preset time; and
   turning off the calibration switching electromagnetic valve, and turning on a water sample inlet regulating electromagnetic valve.

* * * * *